United States Patent
Tsusaka et al.

(10) Patent No.: US 9,381,064 B2
(45) Date of Patent: Jul. 5, 2016

(54) FORCE PRESENTATION APPARATUS, FORCE PRESENTATION METHOD, AND FORCE PRESENTATION PROGRAM

(71) Applicant: Panasonic Corporation, Osaka (JP)

(72) Inventors: Yuko Tsusaka, Osaka (JP); Mikiya Nakata, Nara (JP); Yudai Fudaba, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 215 days.

(21) Appl. No.: 14/021,082

(22) Filed: Sep. 9, 2013

(65) Prior Publication Data

US 2014/0100484 A1 Apr. 10, 2014

(30) Foreign Application Priority Data

Oct. 9, 2012 (JP) ................. 2012-224093

(51) Int. Cl.
| | |
|---|---|
| *A61B 5/00* | (2006.01) |
| *A61B 5/103* | (2006.01) |
| *A61B 5/117* | (2016.01) |
| *A61B 18/14* | (2006.01) |
| *A61B 18/00* | (2006.01) |

(52) U.S. Cl.
CPC ........... *A61B 18/1492* (2013.01); *A61B 5/6885* (2013.01); *A61B 2018/00577* (2013.01)

(58) Field of Classification Search
CPC ............. A61B 5/6885; A61B 18/1492; A61B 2018/00577
See application file for complete search history.

(56) References Cited

U.S. PATENT DOCUMENTS

| | | | | |
|---|---|---|---|---|
| 5,851,172 | A | * 12/1998 | Bueche | ................ A61N 5/1007 600/3 |
| 2007/0142749 | A1* | 6/2007 | Khatib | ..................... A61B 6/12 600/587 |
| 2010/0292566 | A1* | 11/2010 | Nagano | ................ A61B 5/6885 600/424 |

FOREIGN PATENT DOCUMENTS

| | | |
|---|---|---|
| JP | 2000-010467 | 1/2000 |
| JP | 2009-139179 | 6/2009 |
| JP | 2009-162746 | 7/2009 |

\* cited by examiner

*Primary Examiner* — Adam J Eiseman
*Assistant Examiner* — Patrick Fernandes
(74) *Attorney, Agent, or Firm* — Wenderoth, Lind & Ponack, L.L.P.

(57) ABSTRACT

Upon insertion of an insertion member into a living body vessel by an operator, a force individually applied to the living body vessel by the insertion member is measured by a force measuring unit, and based upon the force measured by the force measuring unit, information to be presented to an experiencing person is determined by a determination unit so that based upon the determined information, the corresponding force is presented to the experiencing person by a force presentation unit.

16 Claims, 29 Drawing Sheets

| DEFLECTION AMOUNT L (m) | FORCE (N, Nm) |
|---|---|
| L1 | F1 |
| L2 | f2 |
| .. | .. |
| L100 | F100 |
| ⋮ | ⋮ |

| NUMBER OF MARKS | INSERTION LENGTH |
|---|---|
| M1 | L1 |
| M2 | L2 |
| .. | .. |
| M100 | L100 |
| ⋮ | ⋮ |

| TIME (msec) | FORCE (N,Nm) | INSERTION LENGTH (m) | REFERENCE POINT | INDIVIDUAL FORCE |
|---|---|---|---|---|
| $t_0$ | $f_0$ | $p_0$ | 1 | $fr_0$ |
| $t_{01}$ | $f_{01}$ | $p_{01}$ | 0 | |
| .. | .. | .. | .. | .. |
| $t_1$ | $f_1$ | $p_1$ | 1 | $fr_1$ |
| $t_{11}$ | $f_{11}$ | $p_{11}$ | 0 | |
| .. | .. | .. | .. | .. |
| $t_2$ | $f_2$ | $p_2$ | 1 | $fr_2$ |
| $t_{21}$ | $f_{21}$ | $p_{21}$ | 0 | |
| | ⋮ | ⋮ | | |

Fig.8
| ID | NOTIFICATION INFORMATION DETERMINATION METHOD | FLAG |
|---|---|---|
| 1 | PRESENT INDIVIDUAL FORCE UPON APPLICATION OF LOAD | 1 |
| 2 | PRESENT WITH INCREASED SENSITIVITY UPON APPLICATION OF LOAD | 0 |
Fig.9A
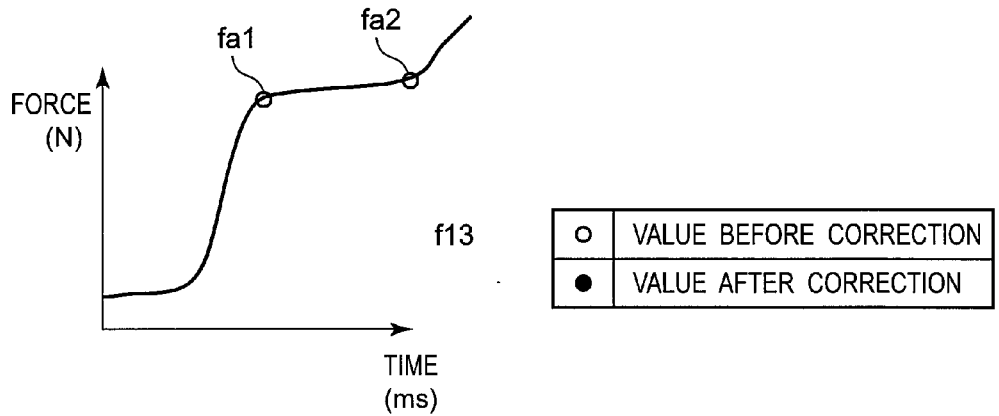
Fig.9B
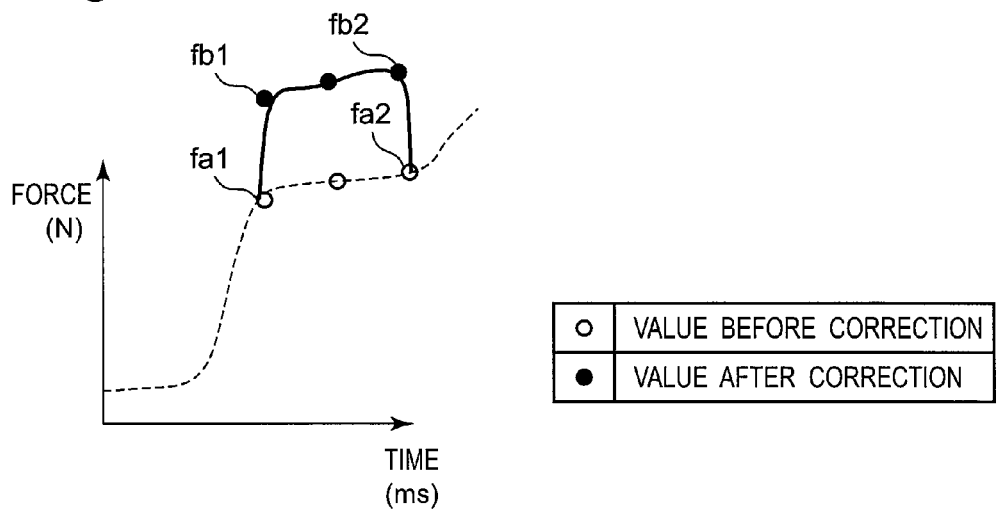

Fig.16

| TIME (msec) | FORCE (N,Nm) | INSERTION LENGTH (m) | INSERTION VELOCITY (m/msec) | REFERENCE POINT | INDIVIDUAL FORCE |
|---|---|---|---|---|---|
| $t_0$ | $f_0$ | $p_0$ | ... | 1 | $fr_0$ |
| $t_{01}$ | $f_{01}$ | $p_{01}$ | $s_{01}$ | 0 | |
| ... | ... | ... | ... | ... | |
| $t_1$ | $f_1$ | $p_1$ | $s_1$ | 1 | $fr_1$ |
| $t_{11}$ | $f_{11}$ | $p_{11}$ | $s_{11}$ | 0 | |
| ... | ... | ... | ... | ... | |
| $t_2$ | $f_2$ | $p_2$ | $s_2$ | 1 | $fr_2$ |
| $t_{21}$ | $f_{21}$ | $p_{21}$ | $s_{21}$ | 0 | |

Fig.17

| ID | NOTIFICATION INFORMATION DETERMINATION METHOD | FLAG |
|---|---|---|
| 1 | PRESENT INDIVIDUAL FORCE WHEN INSERTION VELOCITY IS PREDETERMINED THRESHOLD VALUE OR MORE | 1 |
| 2 | PRESENT WITH INCREASED SENSITIVITY WHEN INSERTION VELOCITY IS PREDETERMINED THRESHOLD VALUE OR MORE | 0 |

Fig.22

| TIME (msec) | FORCE (N,Nm) | INSERTION LENGTH (m) | REFERENCE POINT | INDIVIDUAL FORCE | POSITION OF X-RAY IMAGE CAPTURE DEVICE |
|---|---|---|---|---|---|
| $t_0$ | $f_0$ | $p_0$ | 1 | $fr_0$ | $p_{x1}$ |
| $t_{01}$ | $f_{01}$ | $p_{01}$ | 0 | | $p_{x2}$ |
| ⋮ | ⋮ | ⋮ | ⋮ | ⋮ | ⋮ |
| $t_1$ | $f_1$ | $p_1$ | 1 | $fr_1$ | $p_{x6}$ |
| $t_{11}$ | $f_{11}$ | $p_{11}$ | 0 | | $p_{x7}$ |
| ⋮ | ⋮ | ⋮ | ⋮ | ⋮ | ⋮ |
| $t_2$ | $f_2$ | $p_2$ | 1 | $fr_2$ | $p_{x20}$ |
| $t_{21}$ | $f_{21}$ | $p_{21}$ | 0 | | $p_{x21}$ |
| | ⋯ | ⋯ | | | ⋮ |

Fig.26

| TIME (msec) | FORCE (N,Nm) | INSERTION LENGTH (m) | REFERENCE POINT | INDIVIDUAL FORCE | X-RAY IMAGE |
|---|---|---|---|---|---|
| $t_0$ | $f_0$ | $p_0$ | 1 | $fr_0$ | $x_1$ |
| $t_{01}$ | $f_{01}$ | $p_{01}$ | 0 | | $x_2$ |
| ⋮ | ⋮ | ⋮ | ⋮ | ⋮ | ⋮ |
| $t_1$ | $f_1$ | $p_1$ | 1 | $fr_1$ | $x_6$ |
| $t_{11}$ | $f_{11}$ | $p_{11}$ | 0 | | $x_7$ |
| ⋮ | ⋮ | ⋮ | ⋮ | ⋮ | ⋮ |
| $t_2$ | $f_2$ | $p_2$ | 1 | $fr_2$ | $x_{20}$ |
| $t_{21}$ | $f_{21}$ | $p_{21}$ | 0 | | $x_{21}$ |
| | … | … | | | ⋮ |

Fig.30

| TIME (msec) | FORCE (N,Nm) | INSERTION LENGTH (m) | REFERENCE POINT | INDIVIDUAL FORCE | X-RAY IMAGE | DEGREE OF PREFERENCE |
|---|---|---|---|---|---|---|
| $t_0$ | $f_0$ | $p_0$ | 1 | $fr_0$ | $x_1$ | 1 |
| $t_{01}$ | $f_{01}$ | $p_{01}$ | 0 | | $x_2$ | 1 |
| ⋮ | ⋮ | ⋮ | ⋮ | ⋮ | ⋮ | ⋮ |
| $t_1$ | $f_1$ | $p_1$ | 1 | $fr_1$ | $x_6$ | 2 |
| $t_{11}$ | $f_{11}$ | $p_{11}$ | 0 | | $x_7$ | 2 |
| ⋮ | ⋮ | ⋮ | ⋮ | ⋮ | ⋮ | ⋮ |
| $t_2$ | $f_2$ | $p_2$ | 1 | $fr_2$ | $x_{20}$ | 1 |
| $t_{21}$ | $f_{21}$ | $p_{21}$ | 0 | | $x_{21}$ | 1 |
| ⋯ | ⋯ | ⋯ | | | ⋮ | |

Fig.31

| INSERTION LENGTH (m) | FIRST THRESHOLD VALUE | SECOND THRESHOLD VALUE |
|---|---|---|
| $p_0$ | $ft_{10}$ | $ft_{20}$ |
| $p_{01}$ | $ft_{10}$ | $ft_{20}$ |
| .. | .. | .. |
| $p_1$ | $ft_{11}$ | $ft_{21}$ |
| $p_{11}$ | $ft_{11}$ | $ft_{21}$ |
| .. | .. | .. |
| $p_2$ | $ft_{12}$ | $ft_{22}$ |
| $p_{21}$ | $ft_{12}$ | $ft_{22}$ |
| ⋮ | ⋮ | ⋮ |

FORCE PRESENTATION APPARATUS, FORCE PRESENTATION METHOD, AND FORCE PRESENTATION PROGRAM

BACKGROUND OF THE INVENTION

The technical field relates to a force presentation apparatus for use in measuring a force exerted at the time when an operator inserts an insertion member into a living body vessel and presenting the force to an experiencing person, as well as a force presentation method and a force presentation program for such an apparatus.

In recent years, an operative procedure has been carried out in which by inserting a linear member, such as a guide wire or a catheter, into a vessel of a human body such as a vascular while monitoring its image such as an X-ray radioscopic image or the like so as to carry out a treatment on an angiostenosis portion or the like. Simultaneously as the operator confirms the states of the vessel and/or linear member through captured images thereof, the operator carries out the practice while directly sensing, by his or her hand, force sensitive information of an insertion resistance generated when the linear member is made in contact with the vessel. In this case, however, the force sensitive information that is being directly sensed by the hand of the corresponding operator cannot be directly sensed by other operators. Unexamined Japanese Patent Publication No. 2000-10467 (Patent Document 1) has disclosed a catheter operation simulator by which a catheter insertion is practiced by utilizing a vascular model. In this system, since pieces of objective information, such as an insertion amount or a rotation amount at the time of a catheter insertion and a touch pressure, or the like, can be obtained, it is possible to train unskilled persons while data of the unskilled persons is compared with those of skilled persons.

SUMMARY OF THE INVENTION

Although Patent Document 1 makes it possible to visually display the touch pressure by using a graph or the like, it is not possible to allow an unskilled person to sense a force being directly sensed by the hand of a skilled person by his or her hand of the unskilled person.

One non-limiting and exemplary embodiment provides a force presentation apparatus, force presentation method, and a force presentation program for such an apparatus, each of which estimates individual forces applied to a living body vessel from an insertion member based upon force information measured from the outside of the body and presents the resulting data to an experiencing person.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: a force presentation apparatus comprising:

a force measuring unit that measures a force individually applied to each of portions of the living body vessel by an insertion member when an operator inserts the insertion member into the living body vessel, from outside of the living body vessel in time series;

a determination unit that determines a force to be transmitted to an experiencing person based upon the force measured by the force measuring unit;

a presentation unit that transmits the force determined by the determination unit to the experiencing person; and a force transmission control unit that controls strength of the force to be transmitted by the presentation unit to the experiencing person and timing of switching the strength of the force based upon information of results of measurement in the force measuring unit in time series.

These general and specific aspects may be implemented using a system, a method, and a computer program, and any combination of systems, methods, and computer programs.

In accordance with the force presentation apparatus, the force presentation method, and the force presentation program of the above-mentioned aspect of the present invention, forces to be applied to a living body vessel upon insertion of an insertion member to the living body vessel can be measured for each of individual contact portions in addition to their total value. Moreover, by presenting a force sense detected by the force measuring device to an experiencing person other than the operator, the experiencing person other than the operator is allowed to directly sense the force by his or her hand of the experiencing person.

BRIEF DESCRIPTION OF THE VIEWS

These and other aspects and features of the present disclosure will become clear from the following description taken in conjunction with the embodiments thereof with reference to the accompanying drawings, in which:

FIG. 8 is a view that explains a determination method in a determination unit in accordance with the first embodiment of the present invention;

FIG. 9A is a graph that indicates a force upon insertion of a catheter in accordance with the first embodiment of the present invention;

FIG. 9B is a graph that indicates a force upon insertion of a catheter in accordance with the first embodiment of the present invention;

FIG. 16 is a view that relates to a measuring information database in accordance with the second embodiment of the present invention;

FIG. 17 is a view that explains a determination method in a determination unit in accordance with the second embodiment of the present invention;

FIG. 22 is a view relating to a control information database in accordance with a third embodiment of the present invention;

FIG. 26 is a view relating to a case database in accordance with the force embodiment of the present invention;

FIG. 30 is a view relating to a case database in accordance with the force embodiment of the present invention; and FIG. 31 is a view relating to data of a threshold value of the force measuring device in the first embodiment of the present invention.

DETAILED DESCRIPTION

Figure 1:
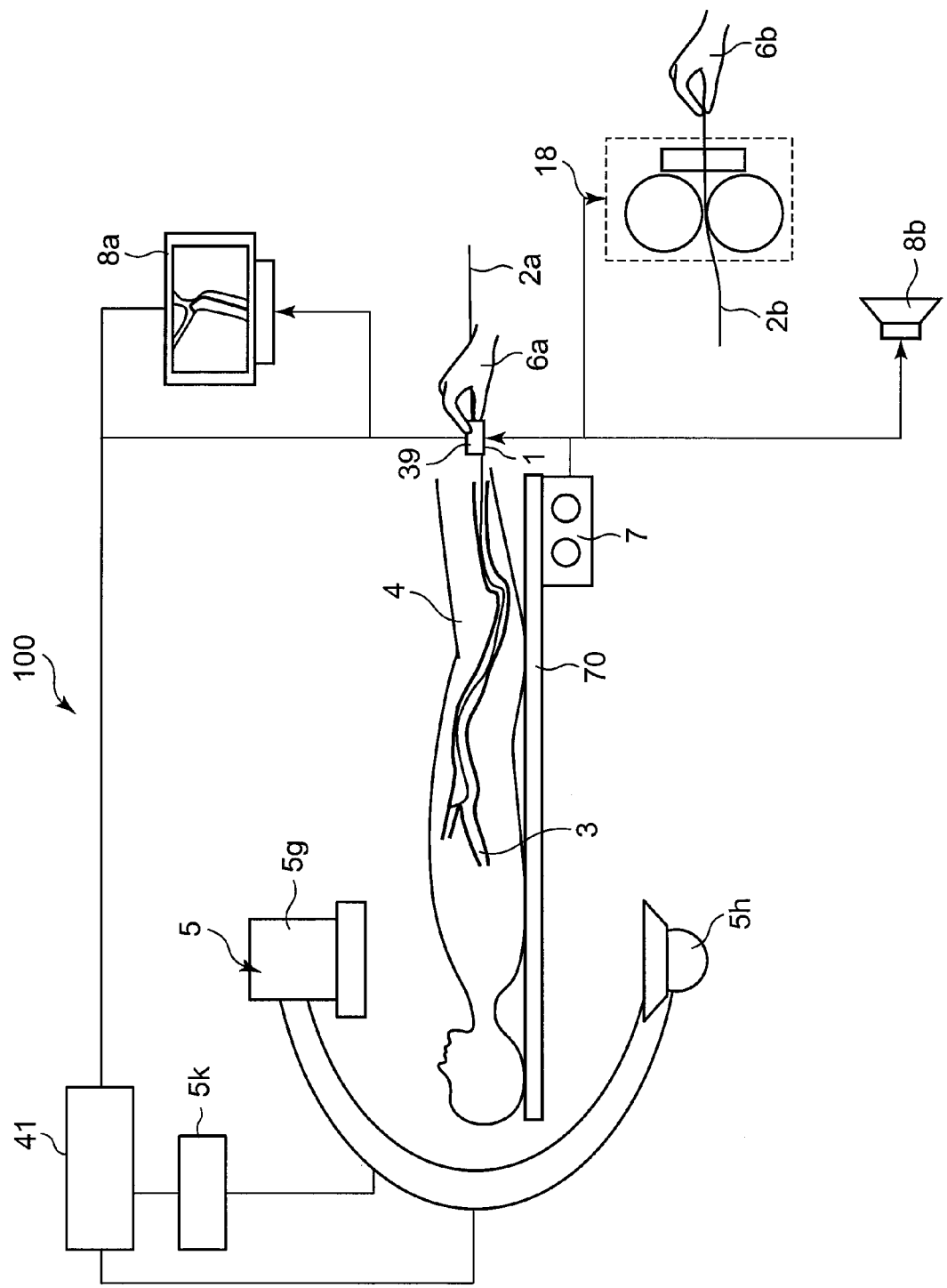
FIG. 1 is a view that shows a schematic configuration of a force presentation system in accordance with a first embodiment of the present invention.

Referring to the drawings, the following description will describe embodiments relating to the present disclosure.

Prior to explaining the embodiments of the present disclosure in detail by reference to the drawings, various aspects of the present disclosure will be explained.

Examples of the disclosed technique are as follows.

1st aspect: A force presentation apparatus comprising:

a force measuring unit that measures a force individually applied to each of portions of the living body vessel by an insertion member when an operator inserts the insertion member into the living body vessel, from outside of the living body vessel in time series;

a determination unit that determines a force to be transmitted to an experiencing person based upon the force measured by the force measuring unit;

a presentation unit that transmits the force determined by the determination unit to the experiencing person; and a force transmission control unit that controls strength of the force to be transmitted by the presentation unit to the experiencing person and timing of switching the strength of the force based upon information of results of measurement in the force measuring unit in time series.

By using the present configuration, it is possible to present a force applied to a living body vessel by an insertion member to an experiencing person different from the operator who is actually inserting the insertion member to the living body vessel.

2nd aspect: The force presentation apparatus according to the 1st aspect, wherein the force measuring unit further comprises:

a force detection unit that detects a force applied to the entire living body vessel by the insertion member, from the outside of the living body vessel;

a point-of-time calculation unit that individually measures a point of time at which the force is applied by the insertion member to the living body vessel, based upon the force detected by the force detection unit; and an individual force calculation unit that individually calculates a force to be applied by the insertion member to the living body vessel, wherein upon insertion of the insertion member into the living body vessel, the point-of-time calculation unit sets a point of time at which a displacement of the force becomes not smaller than a predetermined displacement deciding threshold value for every predetermined insertion length, and the individual force calculation unit divides a value obtained by subtracting information of the force at the point of time immediately before, from information of the force detected by the force detection unit at a measuring point of time, by a number of the points of time that have been set up to the measuring point of time, and adds the resulting divided value to each of individual forces at the respective points of time.

By using the present configuration, it is possible to estimate a force applied to each of individual contact portions from forces measured from the outside of the living body vessel.

3rd aspect: The force presentation apparatus according to the 1st aspect, wherein the determination unit determines so as to present the force to be applied by the insertion member to the entire living body vessel (i) in a case where an individual force applied to the living body vessel is less than a predetermined individual force deciding threshold value, and also determines so as to present a force that is individually applied to the living body vessel and has a greatest difference from a predetermined individual force deciding threshold value among the forces individually applied to the living body vessel that have values not lower than the individual force deciding threshold value, (ii) in a case where an individual force applied to the living body vessel is the predetermined individual force deciding threshold value or more.

By using the present configuration, it is possible to present an appropriate force from forces applied to a living body vessel by an insertion member to an experiencing person different from the operator who is actually inserting the insertion member to the living body vessel.

4th aspect: The force presentation apparatus according to the 1st aspect, wherein the determination unit determines so as to present the force to be applied by the insertion member to the entire living body vessel (i) in a case where an insertion velocity upon insertion by the operator is less than a predetermined insertion velocity-use threshold value, and also determines so as to present a force having a greatest difference from the predetermined insertion velocity-use threshold value among the forces individually applied to the living body vessel that have values not lower than the insertion velocity-use threshold value, (ii) in a case where the insertion velocity is the predetermined insertion velocity-use threshold value or more.

By using the present configuration, it is possible to present an appropriate force from forces applied to a living body vessel by an insertion member to an experiencing person different from the operator who is actually inserting the insertion member to the living body vessel.

5th aspect: The force presentation apparatus according to the 1st aspect, wherein the determination unit determines so as to present the force to be applied by the insertion member to the entire living body vessel with a sensitivity lower than the sensitivity of a measured value that is being measured in the force measuring unit (i) in a case where a force individually applied to the living body vessel has a value less than a predetermined sensitivity adjusting threshold value, and the determination unit also determines so as to present the force to be applied by the insertion member to the entire living body vessel with a sensitivity that is increased from a sensitivity of a measured value that is being measured in the force measuring unit (ii) in a case where a force individually applied to the living body vessel has a value that is the predetermined sensitivity adjusting threshold value or more.

By using the present configuration, it is possible to present an appropriate force from forces applied to a living body vessel by an insertion member to an experiencing person different from the operator who is actually inserting the insertion member to the living body vessel.

6th aspect: The force presentation apparatus according to the 1st aspect, wherein the determination unit determines so as to present the force to be applied by the insertion member to the entire living body vessel with a sensitivity lower than a sensitivity of a measured value that is being measured in the force measuring unit (i) in a case where an insertion velocity upon insertion by the operator is less than a predetermined insertion velocity-use threshold value, and the determination unit also determines so as to present the force to be applied by the insertion member to the entire living body vessel with a sensitivity that is increased from a sensitivity of a measured value that is being measured in the force measuring unit (ii) in a case where the insertion velocity is the predetermined insertion velocity-use threshold value or more.

By using the present configuration, it is possible to present an appropriate force from forces applied to a living body vessel by an insertion member to an experiencing person different from the operator who is actually inserting the insertion member to the living body vessel.

7th aspect: The force presentation apparatus according to the 1st aspect, further comprising:

a force decision unit that decides that in a case where force information individually calculated in the individual force calculation unit has a value that is a predetermined load deciding threshold value or more, a load is applied to the living body vessel or the insertion member.

By using the present configuration, it is possible to decide whether or not a load is applied to the living body vessel or the insertion member.

8th aspect: The force presentation apparatus according to the 1st aspect, further comprising:

an image capture device that captures an image of a portion where the insertion member is inserted in the living body vessel; and a notification unit that adds information of a force individually calculated in the individual force calculation unit or information as a result of decision obtained in the force decision unit to a captured image of the living body vessel or the insertion member, and displays the resulting image.

By using the present configuration, it is possible to display that a load is being applied to the living body vessel or the insertion member, together with an image.

9th aspect: The force presentation apparatus according to the 1st aspect, further comprising:

an output unit that informs the operator of information of an individual force calculated in the individual force calculation unit or information as a result of determination given by the force decision unit by means of a sound or an image.

By using the present configuration, it is possible to inform the operator of the fact that a load is being applied to the living body vessel or the insertion member, by means of a voice or an image.

10th aspect: The force presentation apparatus according to the 1st aspect, wherein the determination unit determines information to be presented based upon information as a result of decision given by the force decision unit, the device further comprising:

an image capture device that captures an image of a portion where the insertion member is inserted in the living body vessel based upon presentation information determined by the determination unit;

an image capture device control unit that controls the image capture device; and a notification unit that adds presentation information determined by the determination unit to an image captured by the image capture device and displays the resulting image, under control of the image capture device control unit.

By using the present configuration, it is possible to display whether or not a load is applied to the living body vessel or the insertion member, together with an image.

11th aspect: A force presentation apparatus comprising:

a force measuring unit that measures a force individually applied to each of portions of the living body vessel by the insertion member when an operator inserts the insertion member into the living body vessel, from outside of the living body vessel in time series;

a determination unit that decides a force to be transmitted to an experiencing person based upon the force measured by the force measuring unit;

a presentation unit that transmits the force determined by the determination unit to the experiencing person;

a force transmission control unit that controls strength of the force to be transmitted by the presentation unit to the experiencing person and timing of switching the strength of the force based upon information of results of measurement in the force measuring unit in time series;

an image capture device that captures an image of a portion where the insertion member is inserted in the living body vessel; and a case data storing unit that stores a force applied by the insertion member to the entire living body vessel or a force individually applied to the living body vessel, measured by the force measuring device upon operation by the operator, and an image of the living body vessel or the insertion member captured by the image capture device as a pair, wherein the determination unit determines a force to be transmitted to the experiencing person based upon the force stored in the case data storing unit.

By using the present configuration, it is possible to store a force applied to a living body vessel upon insertion by the operator so that an experiencing person is allowed to feel the force even when the operator is not present.

12th aspect: A force presentation method comprising:

measuring, by a force measuring unit, a force individually applied to each of the portions of the living body vessel by the insertion member when an operator inserts the insertion member into the living body vessel, from outside of the living body vessel in time series;

determining, by a determination unit, a force to be transmitted to an experiencing person based upon the force measured by the force measuring unit;

transmitting the force determined by the determination unit to the experiencing person, by a presentation unit; and controlling, by a control unit, strength of a force to be transmitted by the presentation unit to the experiencing person and timing of switching the strength of the force based upon information of results of measurement in the force measuring unit in time series.

By using the present configuration, it is possible to present a force applied to a living body vessel by an insertion member to an experiencing person different from the operator who is actually inserting the insertion member to the living body vessel.

13th aspect: A computer-readable recording medium including a force presentation program for allowing a computer to function as:

a determination unit that determines a force to be transmitted to an experiencing person based upon a force measured by a force measuring unit that detects a force individually applied to each of portions of the living body vessel by an insertion member when an operator inserts the insertion member into the living body vessel, from outside of the living body vessel in time series;

a presentation unit that transmits the force determined by the determination unit to the experiencing person; and a force transmission control unit that controls strength of the force to be transmitted by the presentation unit to the experiencing person and timing of switching the strength of the force based upon information of results of measurement in the force measuring unit in time series.

By using the present configuration, it is possible to present a force applied to a living body vessel by an insertion member to an experiencing person different from the operator who is actually inserting the insertion member to the living body vessel.

Referring to the drawings, the following description will describe a first embodiment of the present invention in detail.

(First Embodiment)

The following description will explain an outline of a force presentation system (one example of a force presentation apparatus) 100 in accordance with the first embodiment of the present invention.

FIG. 1 shows a state of a catheter inspection or treatment in which an operator 6a inserts a guide wire 2a that is a linear member as one example of a flexible insertion member toward an affected part of a vascular 3 of a brain, a heart, or the like, which is one example of a living body vessel of a human body 4, from the outside of the body.

A portion on a side opposite to the tip of the guide wire 2a is held by a torque device 39 to be secured thereto, and the operator 6a carries out an insertion operation of the guide wire 2a while holding the torque device.

<<Image Capture Device 5>>

While the operator 6a is inserting the guide wire 2a, an X-ray image capture device 5 serving as one example of an image capture device captures an image of the vascular 3 or the guide wire 2a from the outside of the body, and displays the image captured by the X-ray image capture device 5 on a monitor 8a. The resulting information of the image captured by the image capture device 5 is displayed on a notification unit 8 (monitor 8a), and also stored in a measured information database 9 for every predetermined time (for example, every 4 milliseconds) by utilizing a timer 36 from the image capture device 5 via a database input/output unit 14.

The X-ray image capture device 5 is provided with an X-ray generation unit 5g and an X-ray detection unit 5h relating to the X-ray generation unit 5g. The X-ray generation unit 5g irradiates an image capturing subject portion of a human body 4 on a bed 70 with a radioactive ray (for example, an X-ray), and the X-ray detection unit 5h detects an X-ray image that has passed through the human body 4. The X-ray image detected by the X-ray detection unit 5h is connected to the monitor 8a through an image capture device control unit 41 so that an X-ray image is displayed on the monitor 8a. The image capture device control unit 41 drive-controls an X-ray image capture device moving unit 5k so that the X-ray generation unit 5g and the X-ray detection unit 5h can be moved, if necessary, to a portion where the image capturing process is required. In the following embodiments as well, the same configuration can be adopted.

A force measuring device 1 serving as one example of a force measuring unit is disposed at a tip of the torque device 39, and while the operator 6a is inserting the guide wire 2a, the force measuring device 1 measures a contact force at the time when the guide wire 2a is made in contact with a vascular 3, or a frictional force at the time when the guide wire 2a is made in contact with a meandering portion or a branched portion of the vascular 3, individually in time series and in the case where a load is applied onto the vascular 3, a warning is given by the monitor 8a or a speaker 8b serving as one example of an output unit. While confirming the X-ray image displayed on the monitor 8a, a warning sound from the speaker 8b, a warning given from the force measuring device 1, or the like, the operator 6a carries out the insertion of the guide wire 2a.

A presentation unit 18 transmits the force measured by the force measuring device 1 to an experiencing person 6b. The experiencing person 6*b* is allowed to directly feel the force that is actually felt by the hand of the operator 6*a* through an experience-use (presentation-use) guide wire (hereinafter, referred to as "presentation wire") 2*b* by the presentation unit 18.

Additionally, although the experiencing person 6*b* is allowed to feel the force by the presentation unit 18, the experiencing person 6*b* cannot insert the guide wire 2*a* into the vascular 3 by using the presentation unit 18.

Moreover, an input IF (interface) 7, which is an operation interface for use in instructing a start and a completion of the detection (measurement) by the force measuring device 1, as well as a start and a completion of the presentation unit 18, is constituted by, for example, buttons and the like. Upon receipt of starting instructions for measuring a force by the input IF 7, a force measuring operation in the force measuring device 1 is started by a force measurement control unit 200, while upon receipt of terminating instructions for the force measurement from the input IF 7, the force measuring operation in the force measuring device 1 is terminated by the force measurement control unit 200. Additionally, the force measurement control unit 200 also controls the start and completion of an image capturing operation of the X-ray image capture device 5 through the image capture device control unit 41, based upon the start and terminating instructions for force measurements.

Figure 2:
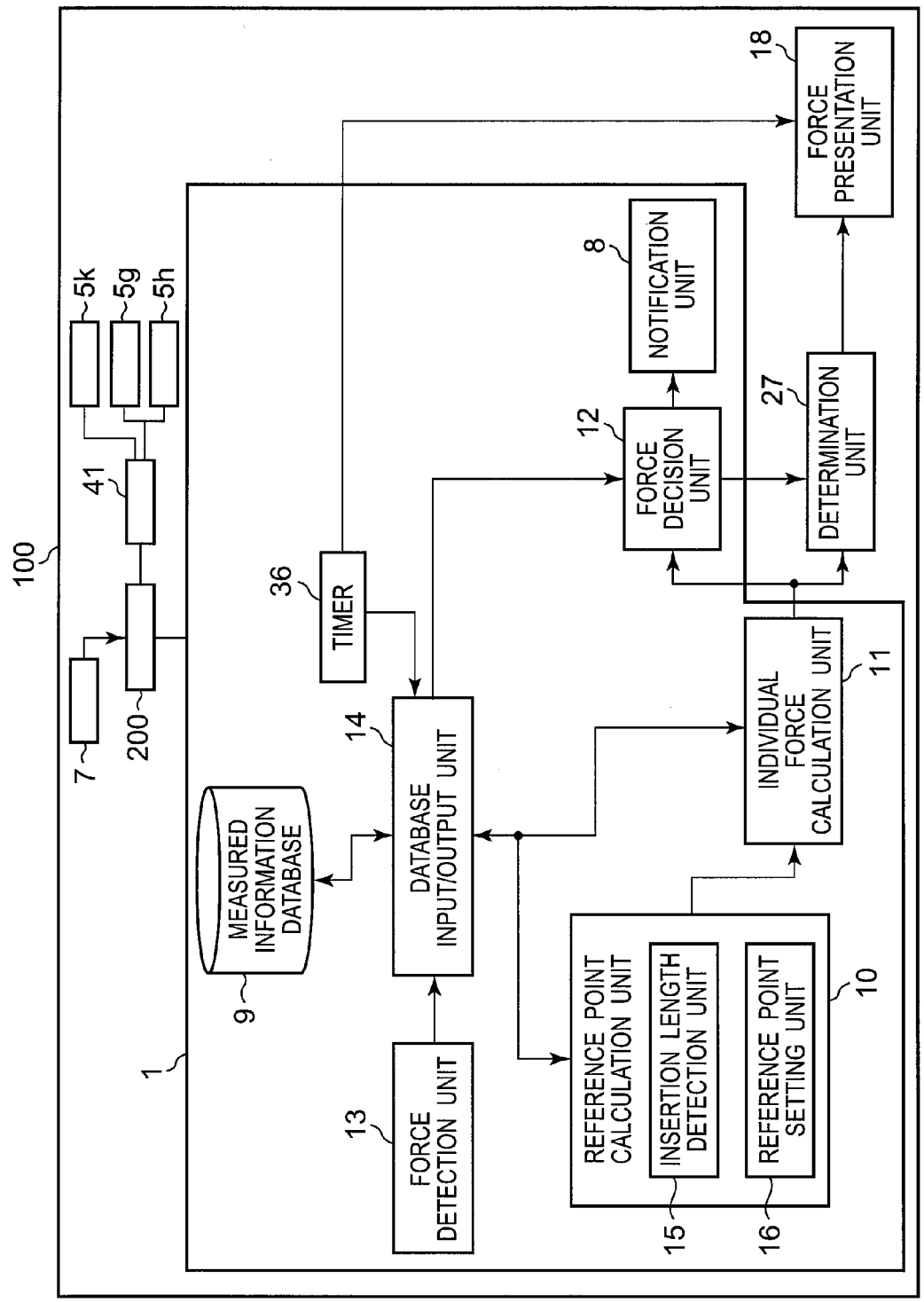
FIG. 2 is a block diagram that shows a detailed configuration of the force presentation system in accordance with the first embodiment of the present invention.

FIG. 2 shows a configuration of a force presentation system 100.

The force presentation system 100 in accordance with a first embodiment is provided with the force measuring device 1, a determination unit 27, and the presentation unit 18.

Figure 3:
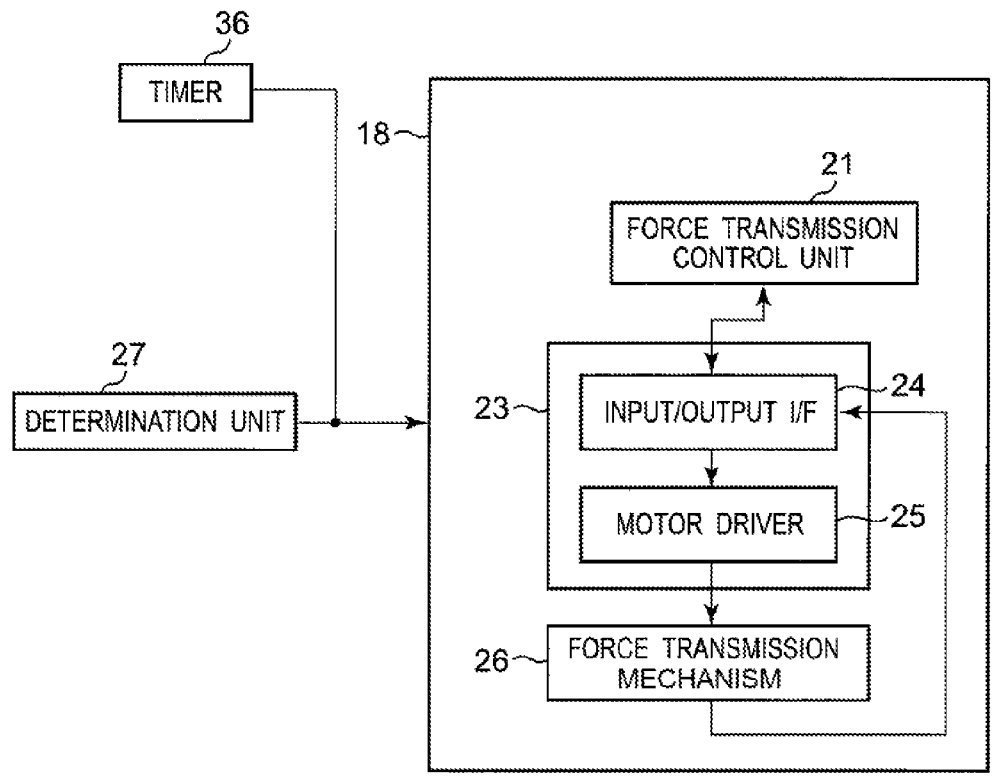
FIG. 3 is a block diagram that shows a detailed configuration of a force presentation apparatus in accordance with the first embodiment of the present invention.

As shown in FIG. 3, the presentation unit 18 is provided with a force transmission control unit 21, a peripheral device 23, and a force transmission mechanism 26. The peripheral device 23 is provided with an input/output IF 24 and a motor driver 25. Detailed descriptions thereof will be given later.

—Force Measuring Device 1—

The force measuring device 1 is provided with a force detection unit 13, the measured information database 9, a timer 36, a database input/output unit 14, a reference point calculation unit 10, an individual force calculation unit 11, a force decision unit 12, and a notification unit 8.

<<Force Detection Unit 13>>

The force detection unit 13 detects a force that is exerted on the guide wire 2*a* at the time when a guide wire 2*a* is made in contact with a vascular 3 from the outside of a human body 4. For example, the force detection unit 13 is constituted by a 6-axis force sensor that measures a force in the insertion direction of the guide wire 2*a* and a force in the rotation direction thereof, and is disposed at a tip of the torque device 39, as shown in FIG. 4A.

The operator 6*a* operates the guide wire 2*a* while holding the torque device 39, and at the time when the guide wire 2*a* is made in contact with meandering portions 3*a* or branched portions 3*b* of the vascular 3, the force detection unit 13 measures forces of the respective meandering portions 3*a* or branched portions 3*b* as a total value, in time series.

Figure 4A:
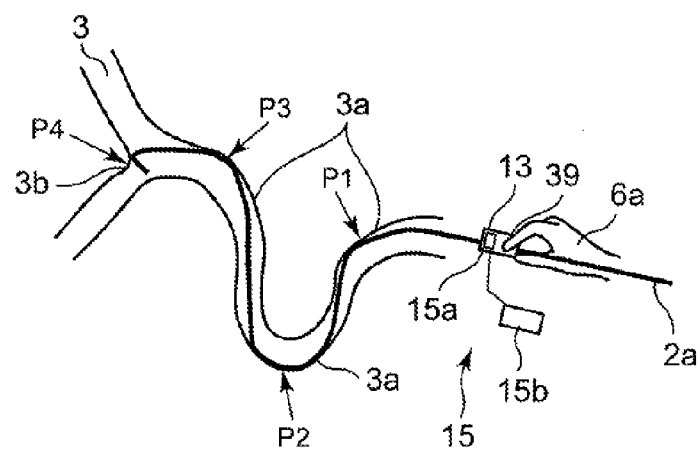
FIG. 4A is a view that shows a schematic configuration of a force measuring device in accordance with the first embodiment of the present invention.

For example, in the case where, as shown in FIG. 4A, forces P1, P2, P3, and P4 are generated at the respective meandering portions 3*a* or branched portion 3*b*, the force detection unit 13 fails to individually detect the respective forces P1, P2, P3, and P4, and measures a total value Pt (in this example, P1+P2+P3+P4=Pt) of the respective forces P1, P2, P3, and P4.

The value of the force Pt to be detected by the force detection unit 13 is detected in time series in the force detection unit 13 for every certain periods of time (for example, every 4 milliseconds) by utilizing the timer 36 to be described later, and the value of the force Pt, thus detected, is outputted from the force detection unit 13 together with the time to the database input/output unit 14 described later, and stored in the measured information database 9 from the database input/output unit 14. This force Pt is a force to be applied onto the entire vascular by the guide wire 2*a*.

Additionally, the force detection unit 13 in the first embodiment is prepared as a 6-axis force sensor; however, this may be prepared as a force sensor capable of measuring two axes of the insertion direction of the guide wire 2*a* and the rotation axis around the insertion direction thereof, or as a force sensor of one axis capable of measuring only the insertion direction of the guide wire 2*a*.

Figure 4B:
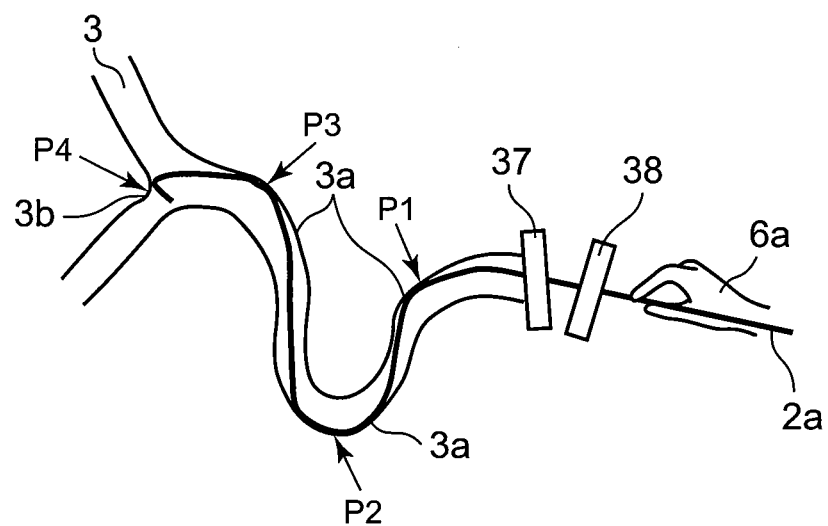
FIG. 4B is a view that shows a schematic configuration of a force measuring device in accordance with the first embodiment of the present invention.
Figure 4C:
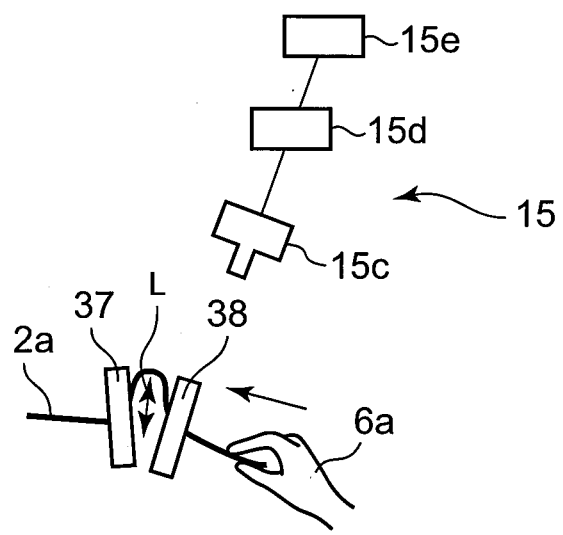
FIG. 4C is a view that shows a schematic configuration of a force measuring device in accordance with the first embodiment of the present invention.

Moreover, the force detection unit 13 is designed to be disposed at the tip of the torque device 39; however, for example, as shown in FIG. 4B, the force detection unit 13 may have a structure in which a guide wire 2*a* is allowed to pass through a first securing unit 37 and a second securing unit 38, and as shown in FIG. 4C, when the operator 6*a* applies a force, a deflection amount (length L in FIG. 4C) between the two first and second securing units 37 and 38 is measured by a laser displacement gauge or an image recognition device 15*c* such as a camera, so that a force corresponding to the deflection amount may be calculated by using an insertion length detection unit-use second calculation unit 15*e* based upon a table (shown in FIG. 4D) indicating the relationship between the deflection amount L and a force, which has been preliminarily prepared, in the insertion length detection unit-use second calculation unit 15*e*.

<<Timer 36>>

After a lapse of a predetermined period of time (for example, every 4 milliseconds), the timer 36 outputs an instruction signal for operating the database input/output unit 14 and the presentation unit 18.

<<Database Input/Output Unit 14>>

The database input/output unit 14 carries out input and output processes of data among the measured information database 9, the force detection unit 13, a reference point calculation unit 10, an individual force calculation unit 11, and the force decision unit 12.

<<Reference Point Calculation Unit 10>>

A reference point calculation unit 10 functions as one example of a time point calculation unit. The reference point calculation unit 10 is provided with an insertion length detection unit 15, and a reference point setting unit 16 that functions as one example of a time point setting unit.

The insertion length detection unit 15 detects an insertion length of the guide wire 2*a* fed into the vascular 3 by the operator 6*a*. For example, as shown in FIG. 4A, the insertion length detection unit 15 is disposed on the torque device 39 that the operator 6*a* operates outside the body. As its specific configuration, the insertion length detection unit 15 is constituted by a distance sensor 15*a* and an insertion length detection unit-use calculation unit 15*b*. By measuring the position of the torque device by using the distance sensor 15*a*, based upon the resulting measured information, the amount of the movement from the position prior to the movement of the torque device 39 is found by the insertion length detection unit-use first calculation unit 15*b* so that the resulting value is detected as an insertion length by the insertion length detection unit-use first calculation unit 15*b*.

Figure 5:
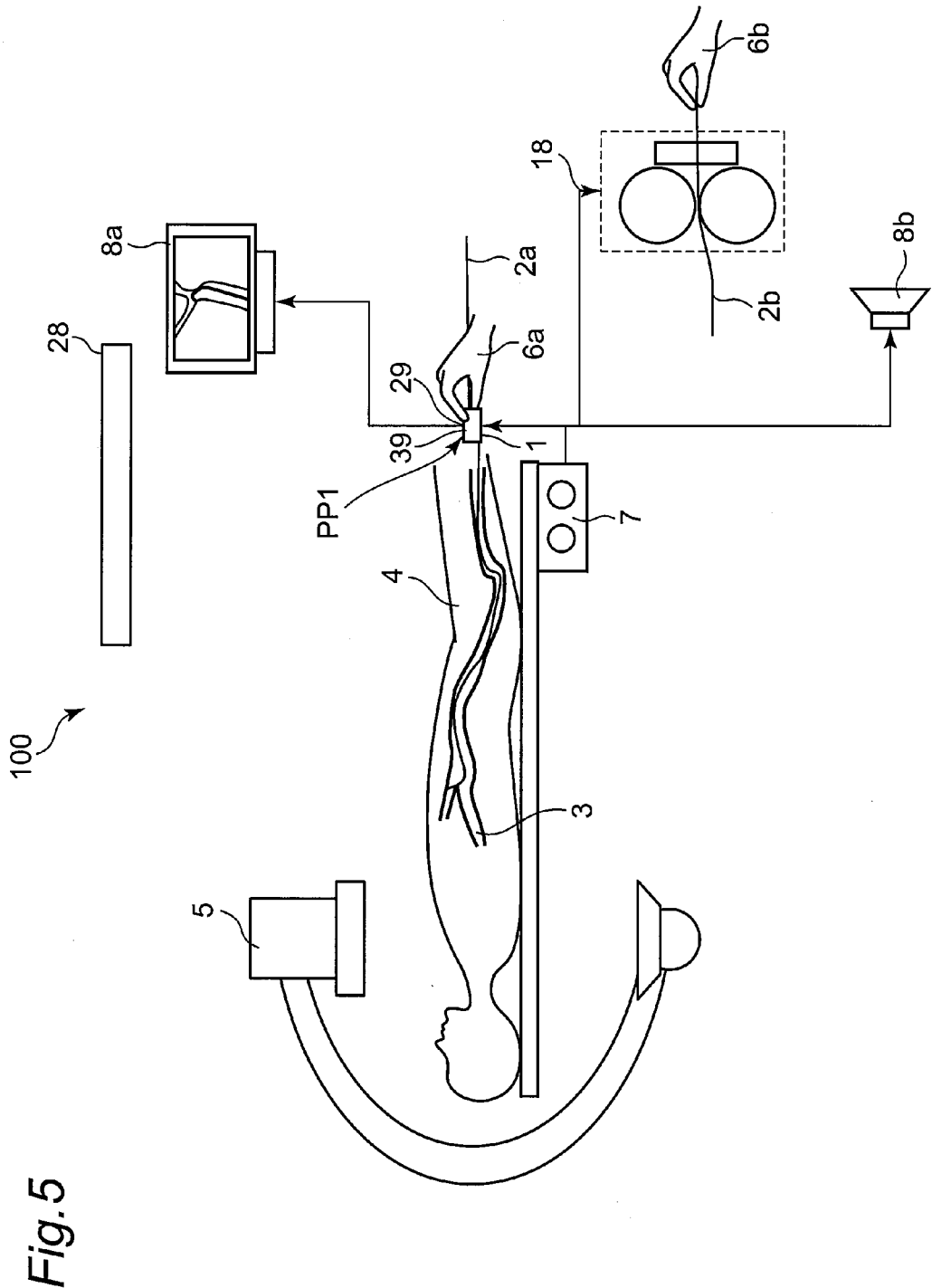
FIG. 5 is a view that explains one example of the insertion length detection unit in accordance with the first embodiment of the present invention.

For example, the distance sensor is prepared as a 3-axis magnetic type position measuring sensor, as shown in FIG. 5. In the magnetic type position measuring sensor, a magnetic force measuring unit 29 is attached to an upper portion (position indicated by PP1 of FIG. 5) of the torque device 39, and the position P1 of the torque device 39 is detected by generating a magnetic field by a magnetic field generating source 28.

Additionally, in the first embodiment, a magnetic type insertion length detection unit 15 is used; however, a marker is disposed on the torque device 39 so that another system in which the position of the torque device 39 is detected by using a camera, or still another system in which the position is detected by using an infrared ray sensor may be used.

Figures 4D, 4E, 4F:
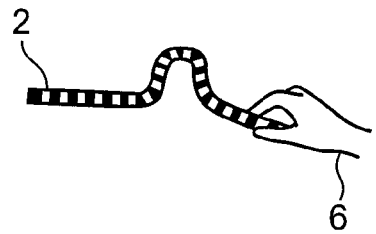
FIG. 4D is a view that shows a correspondence table between a deflection amount and a force of the force measuring device in accordance with the first embodiment of the present invention.
FIG. 4E is a view that shows a schematic configuration of an insertion length detection unit in accordance with the first embodiment of the present invention.
FIG. 4F is a view that shows a correspondence table between the number of marks and the amount of insertion of the insertion length detection unit in accordance with the first embodiment of the present invention.

In the first embodiment, the insertion length detection unit 15 is disposed on the torque device; however, the present invention is not intended to be limited by this configuration. For example, as another example of the insertion length detection unit 15, another system may be used in which, as shown in FIG. 4E, bright and dark marks (for example, white and black marks) are added to the guide wire 2a, and by capturing the number of the marks by a camera, the captured image is image-recognized by an image recognition unit 15d so that the marks are counted by an insertion length detection unit-use second calculation unit 15e and based upon a table (shown in FIG. 4F) that indicates the relationship between the counted marks and the insertion length, the amount of insertion may be detected by the insertion length detection unit-use second calculation unit 15e.

The insertion length detection unit 15 detects the length of the guide wire 2a inserted into the body by utilizing the timer 36 for every predetermined time (for example, every 4 milliseconds) and outputs the resulting data to the database input/output unit 14 together with the time so as to be stored in the measured information database 9.

The reference point setting unit 16 calculates a displacement of the force detected by the force detection unit 13 each time the insertion length detected by the insertion length detection unit 15 is increased or decreased by a predetermined length (for example, 1 mm), and by comparing this with the displacement up to the reference point immediately before, the point of time at which the displacement exceeds a predetermined first threshold value (reference point setting threshold value) (for example, 0.1 N) is set as a reference point. The reference point mentioned here corresponds to a point (point of time for use in measuring individual forces) forming a reference by which each of individual applied forces is individually measured from the total force detected by the force detection unit 13. Additionally, the reference point setting unit 16 sets a point of time at which the insertion length is 0 as the first reference point. The reference point thus set is outputted to the database input/output unit 14 from the reference point setting unit 16, and is stored in the measured information database 9 by the database input/output unit 14. Based upon the total value of the force information detected by the force detection unit 13 and the information of the insertion length detected by the insertion length detection unit 15, the reference point setting unit 16 sets a reference point for use in calculating each of forces exerted at respective points where the guide wire 2a is made in contact with the vascular 3, and the reference point thus set is outputted to the database input/output unit 14 from the reference point setting unit 16.

<<Individual Force Calculation Unit 11>>

Based upon the information from the force detection unit 13 and the information from the reference point calculation unit 10 obtained through the database input/output unit 14, the individual force calculation unit 11 calculates each of individual forces P1, P2, P3, and P4 applied at the respective reference points calculated by the reference point calculation unit 10 from the total value of the force Pt detected by the force detection unit 13, and outputs the resulting forces to the database input/output unit 14 so as to be stored in the measured information database 9.

More specifically, the individual force calculation unit 11 finds values each of which is obtained by subtracting the force information (value) at the reference point immediately before from the force information (value) detected by the force detection unit 13 and then dividing the resulting value by the number of the reference points set before, and by adding the resulting divided value to each of individual forces at the respective reference points, to calculate individual values. The individual forces thus calculated by the individual force calculation unit 11 are outputted to the database input/output unit 14 from the individual force calculation unit 11 together with the reference points.

<<Measured Information Database 9>>

The measured information database 9 stores the information relating to forces detected by the force detection unit 13 and the insertion length detected by the insertion length detection unit 15 together with the corresponding time by utilizing the timer 36 through the database input/output unit 14. Moreover, the individual force calculation unit 11 calculates information relating to the reference points calculated by the reference point calculation unit 10 and information relating to individual forces at the respective reference points calculated by the individual force calculation unit 11, and stores these pieces of information in the measured information database 9 so as to form pairs with the reference points, through the database input/output unit 14. The measured information is inputted/outputted to and from the measured information database 9 through the database input/output unit 14.

Figures 6, 7:
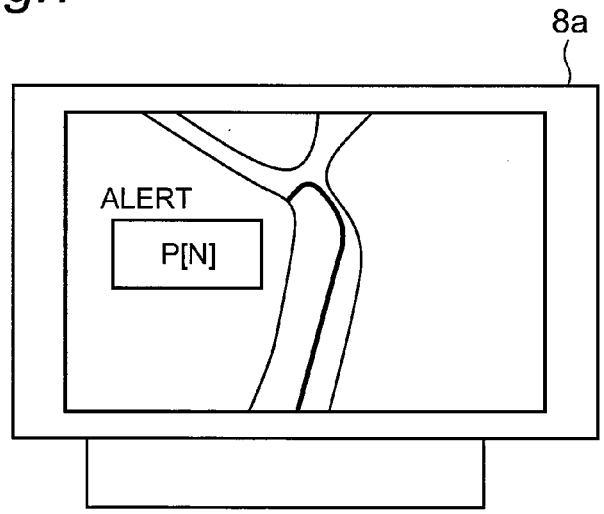
FIG. 6 is a view that relates to a measuring information database in accordance with the first embodiment of the present invention.
FIG. 7 is a view that explains one example of a notification unit in accordance with the first embodiment of the present invention.

FIG. 6 shows one example of the information contents of the measured information database.

(1) The column of "time" indicates information relating to the time during which the insertion task is carried out. In the first embodiment, this is indicated by the unit of millimeter seconds (msec).

(2) The column of "force" indicates information relating to a force detected by the force detection unit 13. In the first embodiment, a force in the insertion direction is indicated by newton (N), and a force in the rotation direction around the insertion direction is indicated by newton meter (Nm).

(3) The column of "insertion length" indicates the insertion length of the guide wire 2a detected by the insertion length detection unit 15. Additionally, in the first embodiment, this is indicated by a meter (m) unit system.

(4) The column of "reference point" indicates the reference point calculated by the reference point calculation unit 10. In the case of setting the reference point, "1" is set in the corresponding time column, while in the case where no reference point is set, "0" is set therein.

(5) The column of "individual force" indicates information relating to a force calculated by the individual force calculation unit 11. In the first embodiment, a force in the insertion direction is indicated by newton (N), and a force in the rotation direction around the insertion direction is indicated by newton meter (Nm).

<<Force Decision Unit 12>>

Based upon information calculated in the individual force calculation unit 11, the force decision unit 12 decides that a load is applied onto the vascular 3 in the case where the force calculated by the individual force calculation unit 11 is a predetermined second threshold value (load decision-use threshold value) (or sensitivity adjusting threshold value) (for example, 0.5 N) or more. In the case where the force calculated by the individual force calculation unit 11 is decided as being less than the predetermined second threshold value, the force decision unit 12 decides that no lead is applied thereto. The information of the decision result is outputted to the notification unit 8 and the determination unit 27 together with the force calculated by the individual force calculation unit 11.

<<Notification Unit 8>>

The notification unit 8 is a device which, based upon information from the force decision unit 12, notifies the operator 6a of information indicating the results decided by the force decision unit 12, and is constituted by a monitor 8a or a speaker 8b. More specifically, as shown in the monitor 8a of FIG. 7 serving as one example of the notification unit 8, a force P[N] detected by the individual force calculation unit 11 is displayed together with an X-ray image captured by the X-ray image capture device 5, and in the case where the force decision unit 12 decides that a load is applied onto the vascular 3, a warning such as "ALERT" is displayed thereon. Moreover, upon decision by the force decision unit 12 that a load is applied onto the vascular 3, a warning sound is given by the speaker 8b that is another example of the notification unit 8 so as to give the warning to the operator 6a.

Determination Unit 27

Based upon the force detected by the force detection unit 13, the individual forces applied to the respective reference points which are calculated by the individual force calculation unit 11, and information relating to the decision results by the force decision unit 12, the determination unit 27 determines information (presentation information) relating to a force to be presented onto the presentation unit 18.

The determination method to be carried out by the determination unit 27 is, for example, either one of two kinds of determination methods as shown in FIG. 8.

With respect to the method of "presenting an individual force when a load is applied", indicated by ID "1" in FIG. 8, the following description will give explanations.

Upon decision by the force decision unit 12 that no load is applied to the vascular 3, the determination unit 27 notifies the presentation unit 18 to present a force detected by the force detection unit 13. Upon decision by the force decision unit 12 that a load is applied to the vascular 3, the determination unit 27 notifies the presentation unit 18 to present a force having the greatest difference from the predetermined second threshold value among respective forces decided by the force decision unit 12 as causing loads onto the vascular 3.

Next, with respect to the method of "presenting a force with an increased sensitivity when a load is applied", indicated by ID "2" in FIG. 8, the following description will give explanations.

Upon decision by the force decision unit 12 that no load is applied to the vascular 3, the determination unit 27 notifies the presentation unit 18 to present a force detected by the force detection unit 13. Upon decision by the force decision unit 12 that a load is applied to the vascular 3, the determination unit 27 notifies the presentation unit 18 to alter a force having the greatest difference from the predetermined second threshold value among respective forces decided by the force decision unit 12 to have a stronger sensitivity by using a method to be described later so as to be easily transmitted to the experiencing person 6b, and then the altered force is presented by the presentation unit 18.

The following description will explain one example of the altering method of the sensitivity.

FIG. 9A is a graph that shows a relationship between a force calculated by the individual force calculation unit 11 and the time. FIG. 9B is a graph that shows a relationship between a force to be transmitted to the presentation unit 18 and the time, indicates forces that are corrected so as to have stronger sensitivities by using a solid line and black dots, and also indicates forces before the correction by using a broken line and white dots.

A period of force information acquired by the force calculation unit 11 (for example, from a point of time of force information (fa1) of FIG. 9A and FIG. 9B) to the next reference point (a point of time of force information (fa2) of FIG. 9A and FIG. 9B) is calculated as "force correction section". By multiplying the value of the force information of this section by fixed times (for example, 1.2 times or the like), the sensitivity is altered. The force information after the correction is given as force information (fb1, fb2) of FIG. 9B. In this example, the sensitivity is increased.

In contrast, upon decreasing the sensitivity, FIG. 9B may be replaced by FIG. 9A. More specifically, by multiplying the value of the force information of the force correction section by fixed times (for example, (1/1.2) times or the like), the sensitivity is altered. While the force information prior to the correction is given as force information (fb1, fb2) of FIG. 9B, the force information after the correction forms force information (fa1, fa2) of FIG. 9A.

The determination method shown in FIG. 8 is supposed to adopt a method described by "1" in its flag column, and upon alternation of the determination method, by inputting "1" in the flag column of the determination method to be desirably adopted, while inputting "0" in the flag column of the determination method not to be adopted, by the use of the input IF 7, the determination method can be altered.

Moreover, in the present embodiment, a force to be presented is determined in response to a load exerted onto the vascular 3; however, another method may be used in which presentation information as to which force is to be presented among a force or respective individual forces applied to the respective reference points calculated by the force or individual force calculation unit 11 is specified by the operator 6a or the experiencing person 6b by using a button serving as one example of the input IF 7, thus specifying as to which is presented between the force and each of the individual forces, or still another specifying method may be used in which by touching a portion displayed on the notification unit, the individual force at the touched portion is presented.

Moreover, in the case where the force decision unit 12 decides that a load is applied onto the vascular 3, the present embodiment is designed to present a force having the greatest difference from the predetermined second threshold value among respective forces decided by the force decision unit 12; however, upon decision by the force decision unit 12 that a load is applied to the vascular 3, the individual force at the reference point calculated by far the last, that is, at the tip of the guide wire 2a or at the vicinity of the tip thereof, may be presented.

Presentation Unit 18

The presentation unit 18 has the configuration shown in FIG. 3 as described earlier, and is a device for use in presenting a force detected by the force measuring device 1 to the experiencing person 6b based upon the notification method determined by the determination unit 27.

<<Force Transmission Control Unit 21>>

The force transmission control unit 21 controls so as to transmit force information determined by the determination unit 27 to the hand of the experiencing person 6b through the presentation unit 18. At this time, the strength or timing of the force to be presented by the force presentation unit 18 can be controlled by the force transmission control unit 21. With respect to the directions in which the force is generated, there are two axes that relate to the insertion direction of the force transmission mechanism 26 of the force presentation unit 18 to be described later and the rotation direction around the axis of the insertion direction. Positional information or force information for use in presenting a force through the control of the force transmission control unit 21 is outputted to the input/output IF 24 from the force transmission control unit 21 for every predetermined periods of time (for example, every 1 millisecond) by utilizing the timer 36.

<<Peripheral Device 23>>

The peripheral device 23 transmits information between the force transmission mechanism 26 and the force transmission control unit 21. The input/output IF 24 outputs positional information or force information from the force transmission control unit 21 to a motor driver 25 for every predetermined periods of time (for example, for every 1 millisecond) by utilizing the timer 36. The motor driver 25 respectively drives motors described below of the force transmission mechanism 26 in a manner so as to follow the positional information or force information from the input/output IF 24.

<<Force Transmission Mechanism 26>>

Figure 10A:
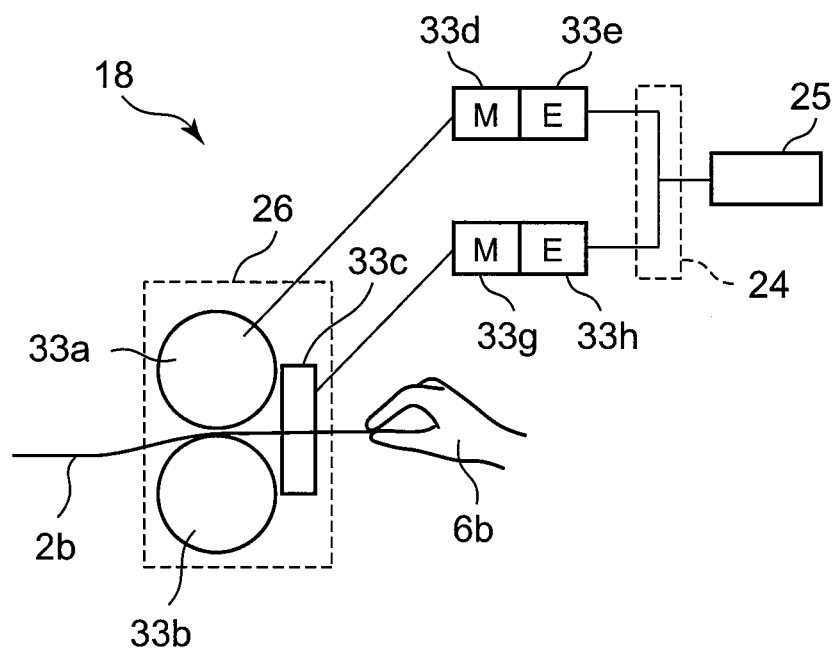
FIG. 10A is a view that explains one example of a force presentation apparatus in accordance with the first embodiment of the present invention.

The force transmission mechanism 26 is a mechanism for use in presenting force information outputted from the force transmission control unit 21 to the experiencing person 6b, and is operated so as to follow positional information or force information outputted from the force transmission control unit 21. As shown in FIG. 10A, its specific example is given by two axes relating to the rotation in the presentation wire insertion direction and the rotation in a direction perpendicular to the insertion direction of the presentation wire. More specifically, a flexible insertion member such as the presentation wire 2b or the like is held by an upper roller (first roller) 33a and a lower roller (second roller) 33b, and by controlling the operations of the rollers 33a and 33b, the presentation wire 2b is fed. In this case, the roller to be controlled may be either one of the upper roller 33a and the lower roller 33b. In the same manner as in a joint portion of a robot arm, a motor 33d and an encoder 33e are disposed on the roller to be controlled so that the motor 33d is controlled by the motor driver 25 in the same manner as in a robot arm. The upper roller 33a and the lower roller 33b are supported by a base unit, not shown, so as to rotate thereon. Moreover, a third roller 33c is prepared therein so that a feeding unit constituted by the upper roller 33a and the lower roller 33b can be rotation-controlled around a center axis, with the insertion direction serving as the center axis, by the third roller 33c. A bracket, not shown, is secured to the third roller 33c, and the upper roller 33a and the lower roller 33c are supported onto the bracket so as to freely rotate thereon. On the third roller 33c, a motor 33g and an encoder 33h are disposed in the same manner as in the joint unit of a robot arm so that the motor 33g is controlled by the motor driver 25 in the same manner as in the robot arm. The third roller 33c is supported onto a base unit, not shown, so as to rotate thereon. Thus, in addition to the insertion direction, the operation of the presentation wire 2b can also be controlled in a rotation direction around a center axis corresponding to the insertion direction. By using this configuration as shown in FIG. 10A, the experiencing person 6b is allowed to have the force presentation in a state where the experiencing person 6b is directly holding the presentation wire 2b.

Figure 10B:
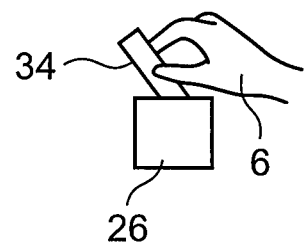
FIG. 10B is a view that explains one example of a force presentation apparatus in accordance with the first embodiment of the present invention.

Additionally, in place of the mechanism of FIG. 10A, the force transmission mechanism 26 may have an arm-type force transmission mechanism in which, as shown in FIG. 10B, an arm (jog stick) 34 capable of being controlled in two axes of the rotation in the presentation wire insertion direction and the rotation in a direction perpendicular to the presentation wire insertion direction is installed.

(Presentation Operation Step of Force Presentation System 100)

Figure 11:
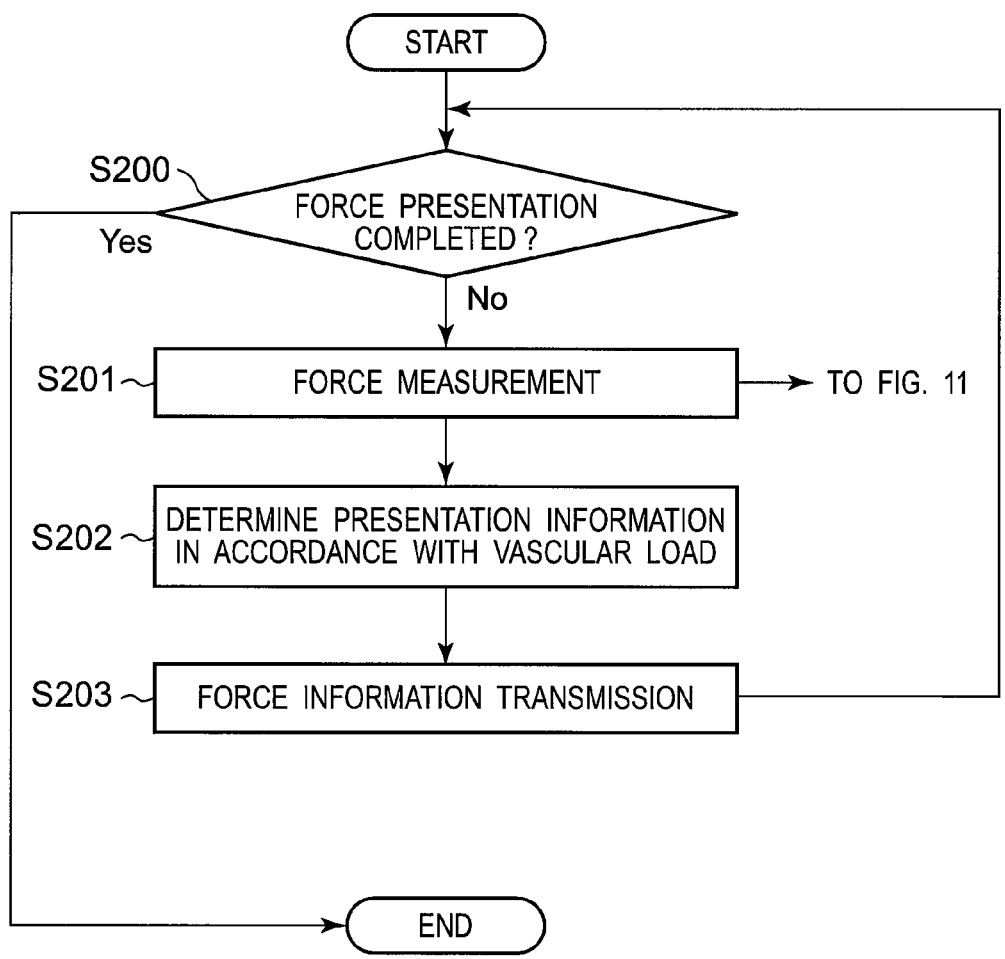
FIG. 11 is a flow chart showing a force presentation system in accordance with the first embodiment of the present invention.
Figure 12:
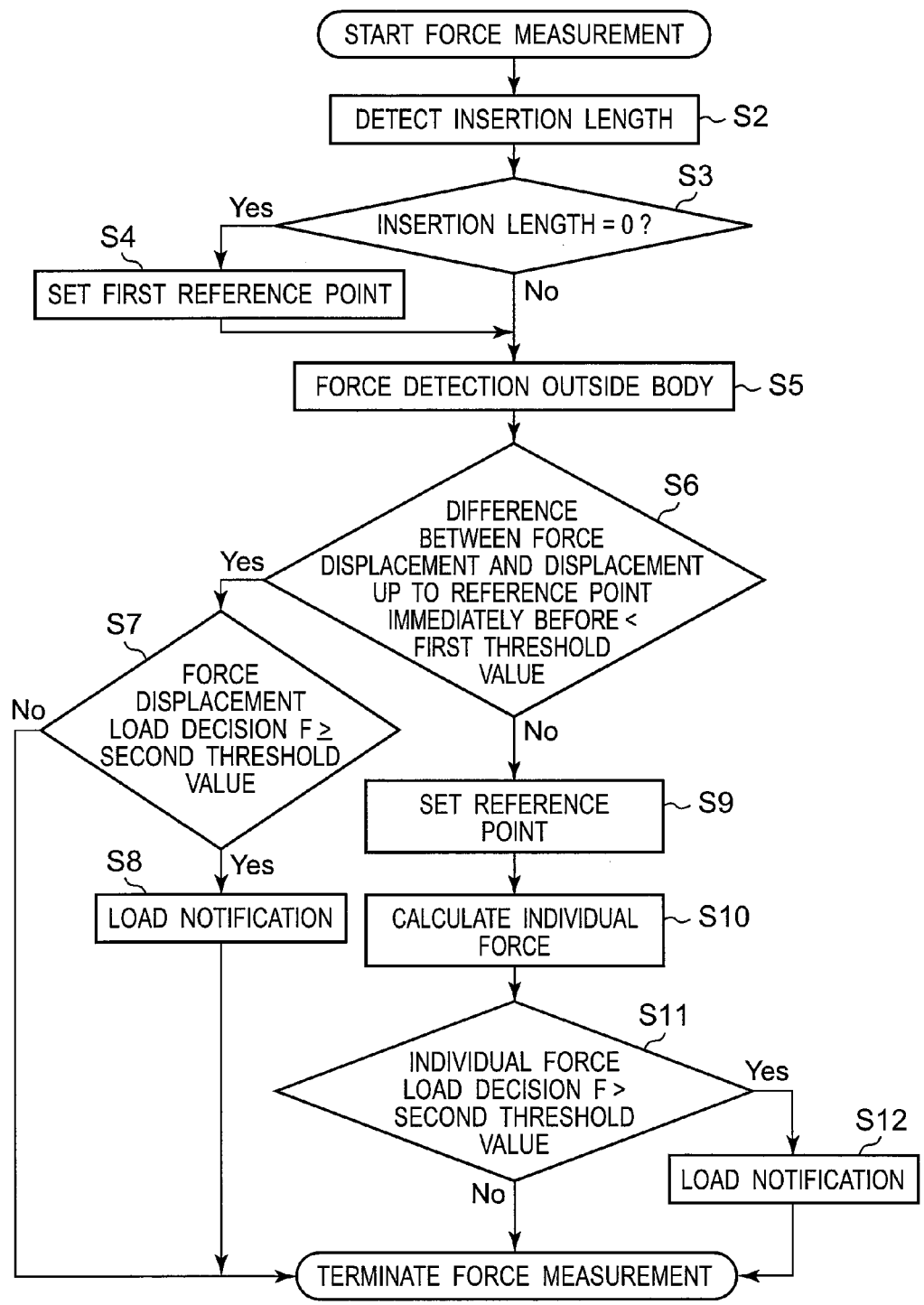
FIG. 12 is a flow chart showing a force measuring device in accordance with the first embodiment of the present invention.

The following description will explain a presentation operation step of the force presentation system 100 in accordance with the first embodiment. FIG. 11 is a flow chart showing the entire force presentation system 100, and FIG. 12 shows a flow chart of the force measuring device 1 that carries out the force measuring process of step S201 of FIG. 11.

In this case, as shown in FIGS. 13(B) to 13(E), an explanation will be given by exemplifying a state in which, when the operator 6a is inserting the guide wire 2a into a meandering vascular 3, a load to be applied to the vascular 3 is presented to the experiencing person 6b.

Figure 13:
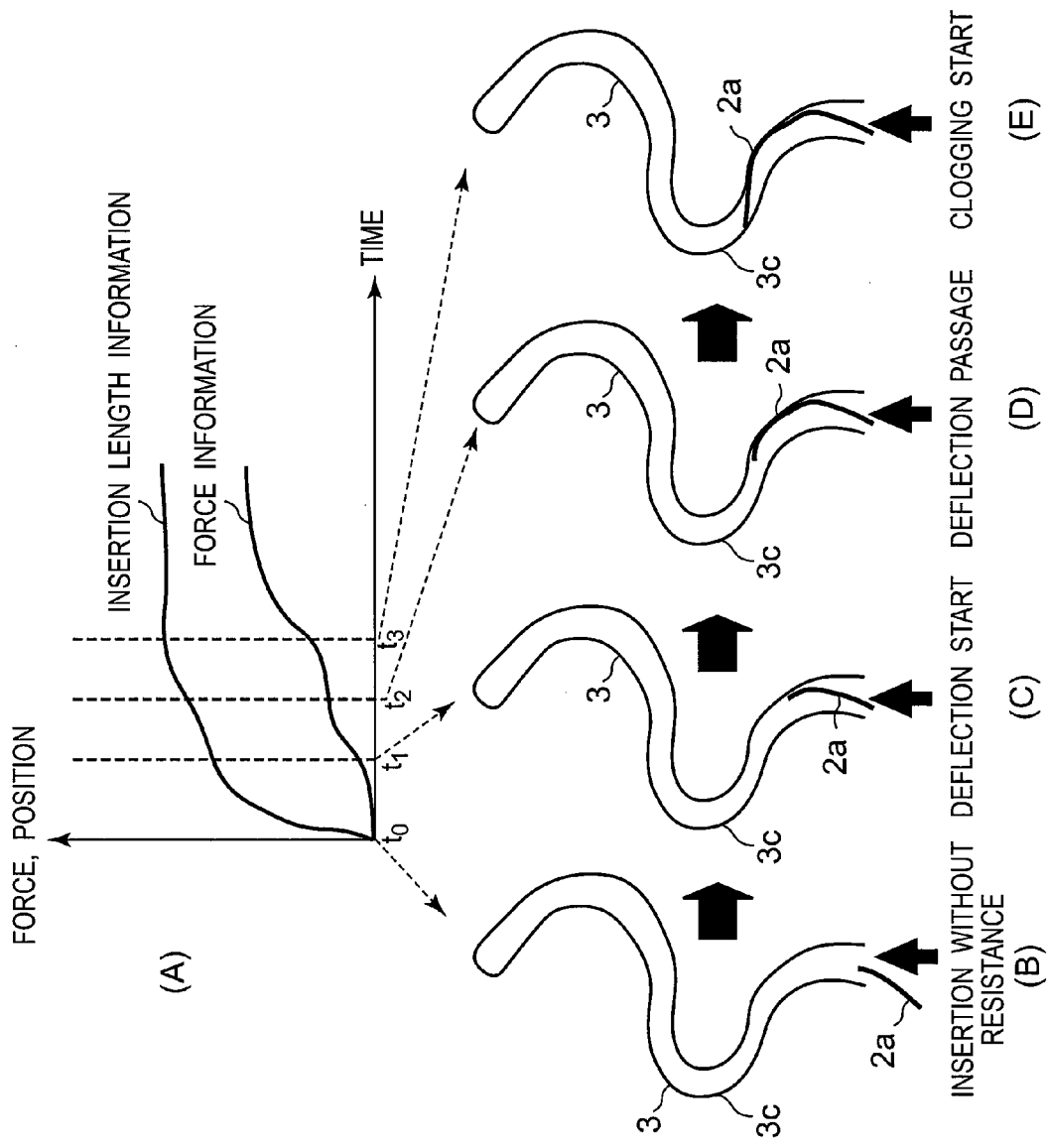
FIG. 13 is an explanatory view that shows catheter insertion operations in accordance with the first embodiment of the present invention, (A) of FIG. 13 is a graph that shows a relationship between a force upon insertion of the catheter and an insertion length; and (B) to (E) of FIG. 13 are views that show the catheter insertion operations.
Figure 14:
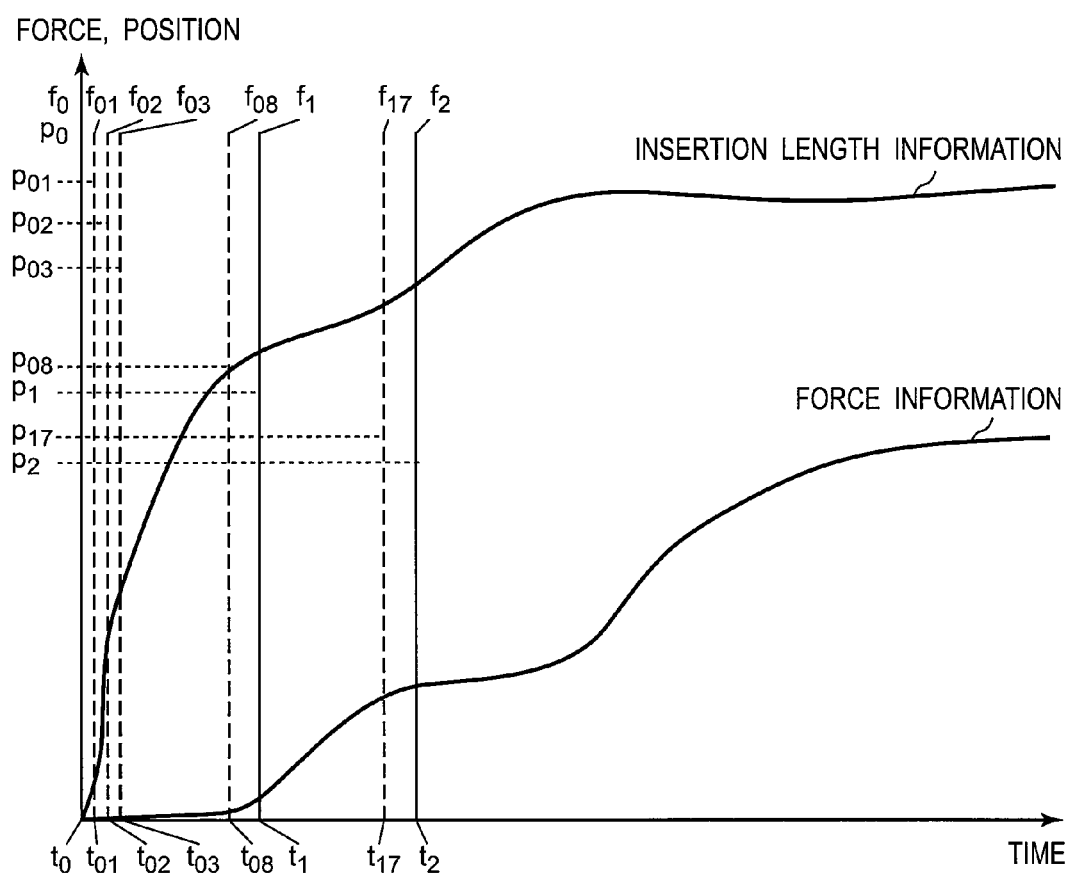
FIG. 14 is a graph that shows a relationship between a force upon insertion of the catheter and an insertion length in accordance with the first embodiment of the present invention.

FIG. 13(A) and FIG. 14 (FIG. 14 corresponds to a graph in which FIG. 13(A) is enlarged) are graphs in which forces, detected by the force detection unit 13 during the insertion tasks shown in FIGS. 13(B) to 13(E), and insertion lengths, detected by the insertion length detection unit 15, are plotted on the axis of abscissa indicating time.

Upon receipt of starting instructions of force measurements and force presentation from the input IF 7, force measurements are started in the force measuring device 1 through the force measurement control unit 200.

(Step S200)

First, in step S200 in FIG. 11, in the case where terminating instructions of force measurements and force presentation is given by the input IF 7, the force measurement in the force presentation system 100 and the force presentation in the force presentation unit 18 are terminated through the force measurement control unit 200. In the case where no terminating instructions of the force measurements and the force presentation is given, the presentation operating process proceeds to step S201.

(Step S201)

Next, in step S201, the force measuring device 1 individually measures a contact force at the time when the guide wire 2a is made in contact with a vascular 3 or a frictional force at the time when the guide wire 2a is made in contact with a meandering portion 3a or a branched portion 3b of the vascular 3, while the operator 6a is inserting the guide wire 2a. Thereafter, the presentation operating process proceeds to step S202.

Referring to a flow chart of FIG. 12, the following description will describe operations of the force measuring device 1 in step S201.

First, the insertion length of the guide wire 2a inserted into the vascular 3 is detected by the insertion length detection unit 15 (step S2).

Next, in the reference point setting unit 16, it is decided whether or not the insertion length detected by the insertion length detection unit 15 is "0" (step S3). In the case where the insertion length detected by the insertion length detection unit 15 is decided as "0" by the reference point setting unit 16, the force measurement operating process proceeds to step S4. In step S4, as shown in FIG. 13(B), with the point of time at which the insertion is started being defined as a first reference point, the reference point setting unit 16 sets reference points (with point of time in FIG. 13(A) being set to "$t_0$"). Moreover, the reference points thus set are outputted from the reference point setting unit 16 to the database input/output unit 14, and stored in the measured information database 9 through the database input/output unit 14 (with the column of the reference point at the point of time $t_0$ in FIG. 6 being indicated by "1"). Thereafter, the force measurement operating process proceeds to step S5.

In contrast, in the case where the insertion length is decided as not "0" by the reference point setting unit 16 in step S3, the force measurement operating process proceeds to step S5.

In step S5, forces to be applied to the guide wire 2a from the outside of the body are detected by the force detection unit 13. Values of forces detected by the force detection unit 13 are outputted to the database input/output unit 14 together with the time by utilizing the timer 36, and stored in the measured information database 9 through the database input/output unit 14. As described above, the forces detected by the force detection unit 13 are measured as the total value of forces in the respective meandering portions 3a or branched portions 3b. Therefore, in step S6 thereafter, the reference points are calculated by the reference point calculation unit 10 and by calculating individual forces at the respective reference points by the reference point calculation unit 10, forces at the respective meandering portions 3a and the like are calculated by the reference point calculation unit 10. Explanations will be successively given below.

In step S6 and thereafter, following step S5, the next reference point is calculated by the reference point setting unit 16 of the reference point calculation unit 10. Each time the insertion length is increased or decreased by a predetermined length (for example, 1 mm), the reference point setting unit 16 calculates a displacement of the force detected by the force detection unit 13. More specifically, a displacement $\Delta f_{01} = f_{01} - f_0$ of the force at a point of time $t_{01}$ when the insertion length is increased by a predetermined length ($p_s = p_{01} - p_0$) in FIG. 14 is calculated by the reference point setting unit 16. The reference point setting unit 16 decides whether or not the displacement $\Delta f_{01}$ of the force is changed with a displacement of the predetermined first threshold value (for example, 0.1 N) or more in comparison with the displacement up to the reference point immediately before (step S6). As in the case of this example, when the reference point setting unit 16 decides that the reference point immediately before corresponds to the first reference point at the point of time ($t_0$), the reference point setting unit 16 decides whether or not the displacement $\Delta f_{01}$ of the force is the predetermined first threshold value (for example, 0.1 N) or more. In the example of FIG. 14, the reference point setting unit 16 decides that the displacement $\Delta f_{01}$ of the force is less than the predetermined first threshold value (for example, 0.1 N), and the point of time $t_{01}$ is not set as the next reference point by the reference point setting unit 16. When the reference point is not set, the force measurement operating process proceeds to step S7.

In step S7, the force decision unit 12 decides whether or not any load is being applied. That is, the force decision unit 12 decides whether or not the displacement $\Delta f_{01}$ of the force is the predetermined second threshold value (for example, 0.5 N) or more. In the case where in step S7, the force decision unit 12 has decided that the displacement $\Delta f_{01}$ of the force is the predetermined second threshold value or more, the force measurement operating process proceeds to step S8.

In step S8, a warning is given to the operator 6a and the like by using the monitor 8a, the speaker 8b, or the like in the notification unit 8, thereby terminating the force measurement operating process.

Additionally, in step S6, displacements of the force detected by the force detection unit 13 are compared each time the insertion length is increased by a predetermined length; however, for example, as shown in FIG. 13(E), there is a case in which the tip of the guide wire 2a is made in contact with a vascular 3 and plugged therein, with the result that even when the guide wire 2a is operated so as to be pushed toward the vascular 3 from the outside of the body, the insertion amount is not changed. In this case, that is, in the case where the insertion length is not changed for a certain period of time or more, displacements of the force detected by the force detection unit 13 are not compared in the reference point setting unit 16 each time the insertion length is increased or decreased by a predetermined length, but displacements of the force detected by the force detection unit 13 are compared in the reference point setting unit 16 each time a predetermined period of time has elapsed.

In the case where, in step S7, the displacement $\Delta f_{01}$ of the force is not the predetermined second threshold value (for example, 0.5 N) or more, the force measurement operating process is terminated.

Next, the force measurement is again started, and after passing through steps S2 to S5, in step S6, the reference point setting unit 16 calculates a displacement $\Delta f_{02} = f_{02} - f_{01}$ of the force at a point of time $t_{02}$ when the insertion length has an increased length $p_{02}$ by a predetermined length ($p_s$) from the insertion length $p_{01}$ in FIG. 14. The reference point setting unit 16 decides whether or not the displacement $\Delta f_{02}$ of the force is changed with a displacement of the predetermined first threshold value (for example, 0.1 N) or more in comparison with the displacement up to the reference point immediately before. In the example of FIG. 14, in the case where the reference point setting unit 16 decides that the displacement $\Delta f_{02}$ of the force is less than the predetermined first threshold value, without the point of time $t_{02}$ being set as the next reference point by the reference point setting unit 16, the force measurement operating process proceeds to step S7 or step S7 and step S8, thereby terminating the force measurement operating process. Successively, the force measurement is started so that the reference point setting unit 16 calculates to find whether or not the reference point can be set with respect to each of points of time $t_{03}$, $t_{04}$, ..., $t_{07}$. In the example of FIG. 14, it is supposed that no reference points have been set by the reference point setting unit 16 up to point of time $t_{08}$.

Next, the force measurement is started, and after passing through steps S2 to S5, in step S6, the reference point setting unit 16 calculates a displacement $\Delta f_{10} = f_1 - f_{08}$ of the force at a point of time $t_1$ when the insertion length is increased by a predetermined length ($p_s = p_1 - p_{08}$). The reference point setting unit 16 decides whether or not the displacement $\Delta f_{10}$ of the force is changed with a displacement of the predetermined first threshold value (for example, 0.1 N) or more in comparison with the displacement up to the reference point immediately before (step S6). In the example of FIG. 14, the reference point setting unit 16 decides that the displacement $\Delta f_{10}$ of the force from the point of time $t_{08}$ to the point of time $t_1$ is the predetermined first threshold value (for example, 0.1 N) or more, and the force measurement operating process proceeds to step S9.

In step S9, the reference point setting unit 16 sets the point of time $t_1$ as the next reference point. Thereafter, the force measurement operating process proceeds to step S10.

In step S10, the reference point set in step S9 is outputted from the reference point setting unit 16 to the database input/output unit 14, and stored in the measured information database 9 through the database input/output unit 14 (with the column of the reference point at the point of time $t_1$ in FIG. 6 being indicated by "1"). In this case, as shown in FIG. 13(C), the reference point at the point of time $t_1$ corresponds to a point of time when the guide wire 2a is made in contact with the wall of the vascular 3 to start causing a deflection.

Next, in step S10, the individual force calculation unit 11 calculates individual forces at the respective reference points. The individual force calculation unit 11 divides a value obtained by subtracting the force information at the reference point immediately before from force information detected by the force detection unit 13, by the number of the reference points that have been set before, and a value thus found is added to an individual force at each of the reference points so that the individual force of each of the reference points is calculated. In this case, however, when the individual force at each of the reference points is a predetermined third threshold value (for example, 0.01 N) or less in the individual force calculation unit 11, that force is not counted as the number of the reference points, and the calculated force is not added to the reference point that has not been counted. More specifically, an explanation will be given by exemplifying the individual force of the reference point at point of time $t_1$ in FIG. 14. A value, obtained by dividing a value $\Delta f_1$ ($=f_1-f_0$) obtained by subtracting a force $f_0$ at the reference point $t_0$ immediately before from a force $f_1$ at the reference point at point of time $t_1$, by the number of the reference points that have been set before (in this example, although "2" is given by the reference points of points of time $t_0$ and $t_1$, the number of reference points becomes "1" because the force $f_0$ at the reference point at point of time $t_0$ is the third threshold value or less), is set as an individual force at the reference point at point of time $t_1$. Additionally, since the force $f_0$ at the reference point at point of time $t_0$ is the third threshold value or less, the addition of the force divided by the number of reference points is not carried out. That is, in this example, an individual force $f_{r1}=\Delta f_1/1$ is given at the reference point at point of time $t_1$. Additionally, an individual force $f_{r0}$ at the reference point of the first point of time $t_0$ is given as a force $f_0$ at the reference point at point of time $t_0$. The individual force $f_{r0}$ calculated in the individual force calculation unit 11 is outputted from the individual force calculation unit 11 to the database input/output unit 14, and stored in the measured information database 9 through the database input/output unit 14 (in this case, individual forces $f_{r0}$ and $f_{r1}$ at points of time $t_0$ and $t_1$ in FIG. 6 are stored).

Next, in step S11, with respect to each of the individual forces calculated by the individual force calculation unit 11, a load deciding process is carried out by the force decision unit 12. More specifically, with respect to each of the individual force $f_{r0}$ at the reference point at point of time $t_0$ previously found and the individual force $f_{r1}$ at the reference point at point of time $t_1$, the force decision unit 12 decides whether or not the force is the second threshold value (for example, 0.5 N) or more. In step S11, in the case where the force decision unit 12 has decided that even any one of these is the second threshold value or more, the force measurement operating process proceeds to step S12.

In step S12, a warning is given to the operator 6a and the like by using the monitor 8a, the speaker 8b, or the like in the notification unit 8, thereby terminating the force measurement operating process. Additionally, when the force decision unit 12 has decided in step S11 that each of these forces is not the second threshold value (for example, 0.5 N) or more, the force measurement operating process is terminated.

In this case, the first threshold value, second threshold value, and third threshold value are prepared as different values depending on the kinds (vascular diameter or portion) or the states of the vascular 3 of a patient (human body 4), and for example, the operator 6a may select the threshold values from plurality of threshold values preliminarily formed, or the operator 6a may input the threshold values to the reference point setting unit 16, the force decision unit 12, or the individual force calculation unit 11 through an input device such as a keyboard, a button, or the like.

Next, referring to FIG. 14, the following description will describe, for example, calculation processes to be carried out in the reference point calculation unit 10 to find a reference point $t_2$ following the reference points to and $t_1$. With the sequence returning to step S1, after again passing through step S2, step S3, and step S5, the reference point calculation unit 10 starts a reference point calculation process. Successively, the reference point setting unit 16 carries out calculations so as to find whether or not a reference point can be set. In the example of FIG. 14, it is supposed that no reference points have been set by the reference point setting unit 16 up to point of time $t_{17}$. The reference point setting unit 16 calculates a displacement $\Delta f_{20}=f_2-f_{17}$ of the force at point of time $t_2$ when the insertion length is increased by a predetermined length (for example, 1 mm) ($p_s=p_2-p_{17}$). The reference point setting unit 16 decides whether or not the displacement $\Delta f_{20}$ of the force is changed with the predetermined first threshold value (for example, 0.1 N) or more in comparison with the displacement up to the reference point immediately before (step S6). In this example, since the reference point immediately before is point of time $t_1$, the reference point setting unit 16 decides whether or not the absolute value of a difference between the displacement $\Delta f_{10}=f_1-f_0$ of the force at reference point at point of time $t_1$ and the displacement $\Delta f_{20}$ of the force is the predetermined first threshold value or more (step S6). In the example of FIG. 14, the reference point setting unit 16 decides that the absolute value of the difference between the displacement $\Delta f_{10}$ of force and the displacement $\Delta f_{20}$ of force is the predetermined first threshold value or more, and point of time $t_2$ is set as the next reference point by the reference point setting unit 16 (step S9). The reference point set by the reference point setting unit 16 is outputted from the reference point setting unit 16 to the database input/output unit 14, and stored in the measured information database 9 through the database input/output unit 14 (with the column of the reference point at point of time $t_2$ in FIG. 6 being indicated by "1"). As shown in FIG. 13(D), at the reference point at point of time $t_2$, the guide wire 2a is made in contact with the vascular 3 to enlarge a deflection, which is this point of time when the guide wire 2a is allowed to pass through the meandering portion 3c.

Next, in step S10, the individual force calculation unit 11 calculates individual forces at the respective reference points. In the same manner as described earlier, the individual force calculation unit 11 divides a value obtained by subtracting the force information at the reference point immediately before from force information detected by the force detection unit 13, by the number of the reference points that have been set before, and the value thus found is added to an individual force at each of the reference points so that the individual force of each of the reference points is calculated. An explanation will be given by exemplifying the individual force at each of reference points at points of time $t_1$ and $t_2$ in FIG. 14. A value, obtained by dividing a value $\Delta f_2$ ($=f_2-f_1$) obtained by subtracting a force $f_1$ at reference point $t_1$ immediately before from a force $f_2$ at the reference point at point of time $t_2$, by the number of the reference points that have been set before (in this example, except for the reference point at point of time $t_0$, the number of reference points is "2" since there are reference points at points of time $t_1$ and $t_2$), is set as an individual force at the reference point $t_2$. In this example, an individual force $f_{r2}$ at the reference point at point of time $t_2$ is given by $f_{r2}=\Delta f_2/2$. Here, an individual force $f_{r0}$ at the reference point at the first point of time $t_0$ is given as force $f_0$ at the reference point at point of time $t_0$. Moreover, an individual force $f_{r1(new)}$ at the reference point at point of time $t_1$ is given as a value obtained by adding $\Delta f_2/2$ to the individual force (referred to as $f_{r1(old)}$) calculated earlier, that is, $f_{r1(new)}=f_{r1(old)}+\Delta f_2/2$. Each of the individual forces thus calculated in the individual force calculation unit 11 is outputted from the individual force calculation unit 11 to the database input/output unit 14, and stored in the measured information database 9 through the database input/output unit 14 (in this example, individual forces $f_{r0}$, $f_{r1}$ and $f_{r2}$ at points of time $t_0$, $t_1$ and $t_2$ in FIG. 6 are stored).

Next, in step S11, with respect to each of the individual forces calculated by the individual force calculation unit 11, a load deciding process is carried out by the force decision unit 12. More specifically, with respect to each of the individual force $f_{r0}$ at the reference point at point of time $t_0$, the individual force $f_{r1}$ at the reference point at point of time $t_1$, and the individual force $f_{r2}$ at the reference point at point of time $t_2$ that have been found earlier, the force decision unit 12 decides whether or not the force is the second threshold value (for example, 0.5 N) or more (step S11). In step S11, in the case where the force decision unit 12 has decided that even any one of the three individual forces is the second threshold value (for example, 0.5 N) or more, a warning is given to the operator 6a by the monitor 8a, the speaker 8b, or the like of the notification unit 8, thereby terminating the measurement operating process (step S12). In the case where in step 11, the force decision unit 12 has decided that none of the three individual forces are the second threshold value or more, the measurement operating process is terminated.

The descriptions given above are explanations of the force measuring operation of step S201 in FIG. 11.

(Step S202)

Next, the determination unit 27 (step S202 of FIG. 11) determines pieces of information relating to forces to be presented on the presentation unit 18 based upon pieces of information relating to forces detected by the force detection unit 13, respective forces applied to the respective reference points calculated by the individual force calculation unit 11, and decision results of the vascular load decided by the force decision unit 12. Thereafter, the presentation operating process proceeds to step S202.

(Step S203)

In step S203, pieces of force information determined in step S202 are outputted to the force transmission control unit 21 of the presentation unit 18, and the force information is transmitted to the hand of the experiencing person 6b by the force transmission mechanism 26, with the strength and timing of the force to be presented to the experiencing person 6b through the force transmission mechanism 26 being controlled by the force transmission control unit 21. Thereafter, the presentation operating process returns to step S200.

In this case, upon controlling the strength and timing, since upon switching a force (total value of force, that is, total force) to an individual force, a large force is drastically changed to a small force, the force to be presented is corrected and controlled so as to be gradually switched, or the switching timing is controlled so as not to be drastically switched and so as to be switched with a certain fixed period of time (for example, 10 milliseconds). With these controlling processes, it is possible to prevent the experiencing person 6b from failing to support the presentation wire 2b due to a rapid switching or from feeling a force greater than that which has been assumed.

Additionally, in the case where in response to the load, a force to be presented is determined by the determination unit 27 and the force is presented by the presentation unit 18, at the timing in which the force detected by the force detection unit 13 is switched to each force applied to each of the reference points calculated by the individual force calculation unit 11, a sound indicating the switched state may be given by the speaker 8b.

<<Effects of First Embodiment>>

As described above, the first embodiment makes it possible to estimate a load to be applied to the individual vascular 3 at point of time when the guide wire 2a inserted by the operator 6a is made in contact with a vascular 3 or point of time when the guide wire 2a passes through a certain meandering portion, and also to display the presence or absence of the detected force or load on the monitor 8a or the like by the notification unit 8. Moreover, in response to the load applied to the vascular 3, the corresponding force is directly presented to the experiencing person 6b by using the determination unit 27.

(Second Embodiment)

A second embodiment of the present invention relates to an example in which the force presentation method is altered in accordance with an insertion velocity.

In the same manner as in the first embodiment, as shown in FIG. 1, the following description will explain the example in which upon insertion of the guide wire 2a into a vascular 3 by the operator 6a, the corresponding force is measured and presented to the experiencing person 6b.

A force measuring device 1B in accordance with the second embodiment of the present invention is provided with a force detection unit 13, a timer 36, an individual force calculation unit 11, a force decision unit 12, a notification unit 8 and a presentation unit 18, that are the same basic structure as that of the first embodiment; therefore, the explanations of the common portions will be omitted, and the following description will describe only portions different therefrom.

Figure 15:
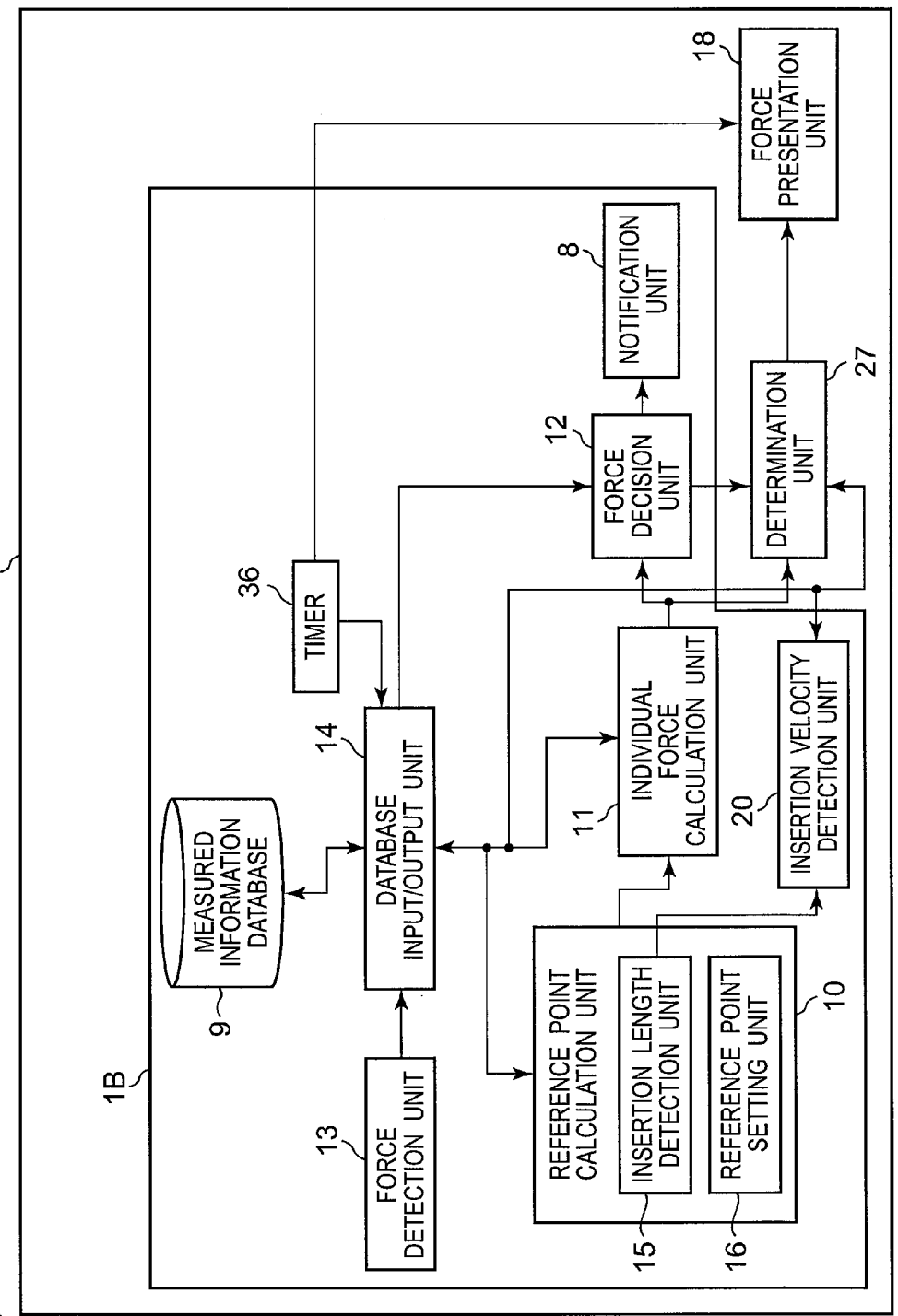
FIG. 15 is a block diagram that shows a detailed configuration of the force presentation system in accordance with a second embodiment of the present invention.

FIG. 15 is a block diagram showing a force presentation system 100B in accordance with the second embodiment. Additionally, portions that are in common with the first embodiment, such as a force measurement control unit 200 and the like, are omitted therefrom.

<<Reference Point Calculation Unit 10>>

A reference point calculation unit 10 is provided with an insertion length detection unit 15, and a reference point setting unit 16 that functions as one example of a point-of-time setting unit. Since the reference point setting unit 16 has the same functions as those of the first embodiment, the description thereof will be omitted. The insertion length detection unit 15 detects the insertion amount by using the same system as that of the first embodiment, outputs the resulting amount to the individual force calculation unit 11 and an insertion velocity detection unit 20, and further records the resulting amount in a measured information database 9 through a database input/output unit 14 for every predetermined period of time (for example, every 4 milliseconds) by utilizing the timer 36.

<<Insertion Velocity Detection Unit 20>>

The insertion velocity detection unit 20 calculates an insertion velocity of the guide wire 2a. The insertion velocity of the guide wire 2a is calculated by the insertion velocity detection unit 20 based upon the insertion length and the corresponding time recorded in the measured information database 9 together with the time. More specifically, supposing that an insertion length is $p_1$ at time $t_1$ and that an insertion length is $p_2$ at time $t_2$, the insertion velocity detection unit 20 calculates the velocity as velocity $s=(p_2-p_1)/(t_2-t_1)$. The insertion velocity calculated by the insertion velocity detection unit 20 is stored in the measured information database 9 together with the time from the insertion velocity detection unit 20 via the database input/output unit 14, by utilizing the timer 36.

<<Measured Information Database 9>>

The measured information database 9 stores the information relating to forces detected by the force detection unit 13, the insertion length detected by the insertion length detection unit 15, and the velocity detected by the insertion velocity detection unit 20 together with the time by utilizing the timer 36.

Moreover, information relating to reference points calculated by the reference point calculation unit 10 and information relating to individual forces at the respective reference points calculated by the individual force calculation unit 11 are stored in the measured information database 9 as pairs together with the reference points.

The measured information to be stored in the measured information database 9 or that have been stored therein is inputted/outputted by the database input/output unit 14.

FIG. 16 shows one example of the contents of information in the measured information database 9.

(1) The column of "time" indicates information relating to the time during which the insertion task is carried out. In the second embodiment, this is indicated by the unit of millimeter seconds (msec).

(2) The column of "force" indicates information relating to a force detected by the force detection unit 13. Additionally, in the second embodiment, a force in the insertion direction of the guide wire 2a is indicated by newton (N), and a force in the rotation direction around the insertion direction is indicated by newton meter (Nm).

(3) The column of "insertion length" indicates the insertion length of the guide wire 2a detected by the insertion length detection unit 15. Additionally, in the second embodiment, this is indicated by a meter (m) unit system.

(4) The column of "insertion velocity" indicates the insertion velocity of the guide wire 2a detected by the insertion velocity detection unit 20. Additionally, in the second embodiment, this is indicated by the meter per millisecond (m/millisecond) unit system.

(5) The column of "reference point" indicates the reference point calculated by the reference point calculation unit. In the case of setting the reference point, "1" is set in the corresponding time column, while in the case of setting no reference point, "0" is set therein.

(6) The column of "individual force" indicates information relating to a force calculated by the individual force calculation unit 11. Additionally, in the second embodiment, a force in the insertion direction of the guide wire 2a is indicated by newton (N), and a force in the rotation direction around the insertion direction is indicated by newton meter (Nm).

<<Database Input/Output Unit 14>>

The database input/output unit 14 carries out data input/output operations among the measured information database 9, the force detection unit 13, the reference point calculation unit 10, the individual force calculation unit 11, the force decision unit 12, and the insertion velocity detection unit 20.

<<Determination Unit 27>>

The determination unit 27 determines information relating to a force to be presented onto the presentation unit 18 based upon the force detected by the force detection unit 13, the respective individual forces applied to the respective reference points, which are calculated by the individual force calculation unit 11, and the insertion velocity detected by the insertion velocity detection unit 20.

As the determination method by the determination unit 27, for example, either one of two kinds of the determination methods as shown in FIG. 17 may be used.

First, the following description will explain a method of "presenting an individual force in the case where the insertion velocity is a threshold value or more" as indicated by ID "1" in FIG. 17.

In the case where the determination unit 27 determines that the insertion velocity detected in the insertion velocity detection unit 20 is less than (for example, less than 0.004 m/s) a predetermined fourth threshold value (insertion velocity threshold value), the determination unit 27 notifies the presentation unit 18 to present the force detected by the force detection unit 13.

In the case where the determination unit 27 has determined that the insertion velocity detected by the insertion velocity detection unit 20 is the predetermined fourth threshold value (for example, 0.004 m/s or more) or more, the determination unit 27 notifies the presentation unit 18 to present a force having the greatest difference from the predetermined fourth threshold value, among the respective forces decided by the force decision unit 12.

Next, the following description will explain a method of "presenting an individual force with an increased sensitivity in the case where the insertion velocity is a threshold value or more" as indicated by ID "2" in FIG. 17.

In the case where the determination unit 27 determines that the insertion velocity detected in the insertion velocity detection unit 20 is less than (for example, less than 0.004 m/s) the predetermined fourth threshold value, the determination unit 27 notifies the presentation unit 18 to present the force detected by the force detection unit 13. In the case where the determination unit 27 has determined that the insertion velocity detected by the insertion velocity detection unit 20 is the predetermined threshold value (for example, 0.004 m/s or more) or more, the determination unit 27 notifies the presentation unit 18 to present a force having the greatest difference from the predetermined fourth threshold value, among the respective forces decided by the force decision unit 12, with its sensitivity being altered so as to become stronger and to be easily transmitted to the experiencing person 6b, by using a method to be described later. The strength of the sensitivity is controlled by the same method as that of the first embodiment.

(Presentation Operating Step of Force Presentation System 100B)

Figure 18:
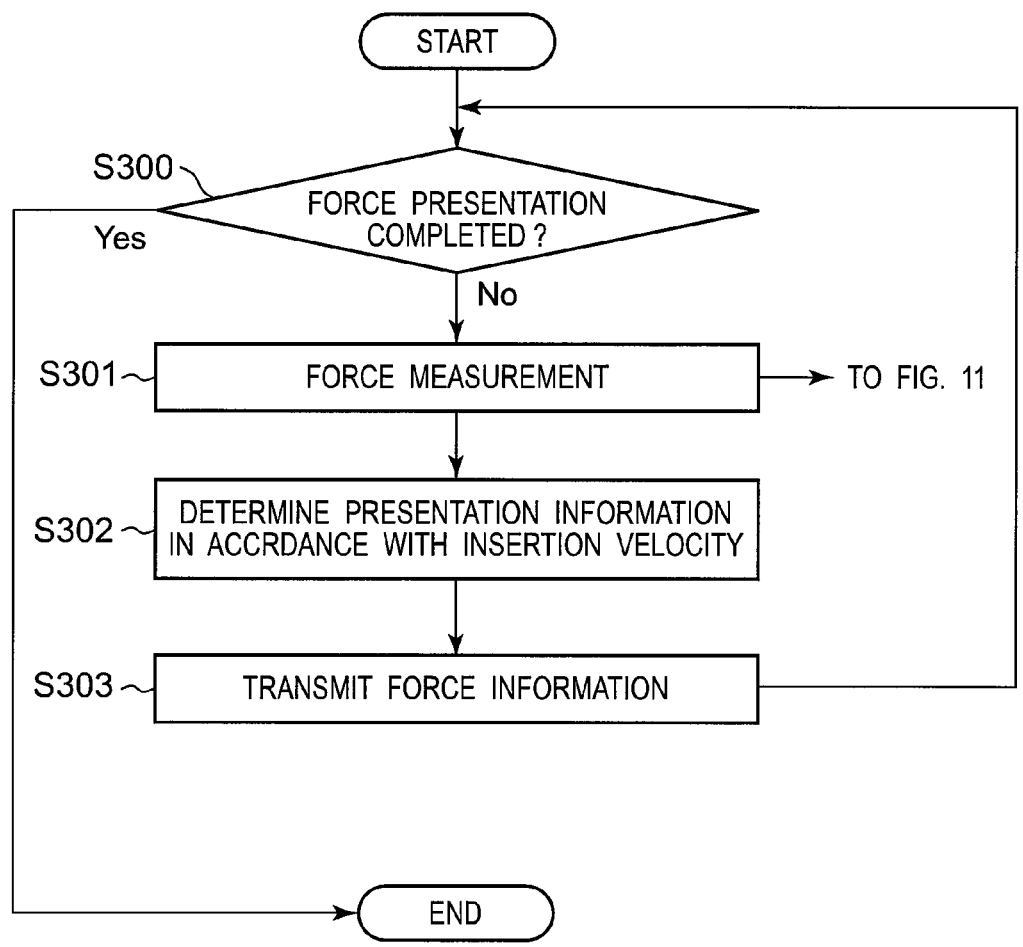
FIG. 18 is a flow chart showing a force presentation system in accordance with the second embodiment of the present invention.

The following description will describe a presentation operating step of the force presentation system 100B of the second embodiment. FIG. 18 is a flow chart of a presentation unit 1B of the second embodiment.

Upon receipt of starting instructions for measuring a force and for presenting a force by the input IF 7, the force measuring operation in a force measuring device 1B is started by the force measurement control unit 200.

(Step S300)

First, in step S300 in FIG. 18, upon receipt of terminating instructions of the force measurement and force presentation by the input IF 7, the force measurement and force presentation of the presentation unit 18 in the force presentation system 100B are terminated by the force measurement control unit 200. In the case of no terminating instructions of the force measurement and force presentation, the presentation operating process proceeds to the next step S301.

(Step S301)

Next, in step S301, upon insertion of a guide wire 2a by the operator 6a, the force measuring device 1B individually measures a contact force when the guide wire 2a is made in contact with the vascular 3 or a frictional force when the guide wire 2a is made in contact with a meandering portion 3a or a branched portion 3b of the vascular 3. Since the measuring method is the same as that of the first embodiment, the description thereof will be omitted. Moreover, when the guide wire 2a is further made in contact with the vascular 3, force information and an insertion velocity are outputted by the force measuring device 1B, the force detection unit 13, and the insertion velocity detection unit 20. Thereafter, the presentation operating process proceeds to the next step S302.

(Step S302)

Next, based upon the force detected by the force detection unit 13, the individual forces applied to the respective reference points, which are calculated in the individual force calculation unit 11, and the insertion velocity, the determination unit 27 (step S302) determines information relating to a force to be presented onto the presentation unit 18. Normally, in the case of a portion of the vascular 3 having a thick inner diameter or a portion having less meandering parts, since the insertion task of the guide wire 2a by the operator 6a is not difficult so much, the insertion velocity of the guide wire 2a becomes faster. In contrast, in the case of a portion of the vascular 3 having a narrow inner diameter, or a portion having more meandering parts, or a portion having a disorder such as an aneurism, the insertion velocity of the guide wire 2a by the operator 6a becomes slower since attention needs to be taken in inserting the guide wire 2a. Therefore, in the case where the insertion velocity is slower, the force to be applied to the vascular 3 needs to be sensed more carefully than in the case where the insertion velocity is faster, and moreover, a portion such as a tip of the guide wire 2a where a medical procedure is actually exerted needs to be more carefully sensed. For this reason, the determination unit 27 determines information relating to a force to be presented onto the presentation unit 18 in a manner so as to present a weak sensitivity of the total force or the force at the portion in which the insertion velocity is fast, with a stronger sensitivity of the individual force or the force being exerted at the portion in which the insertion velocity is slow in comparison with the portion in which the insertion velocity is fast. Thereafter, the presentation operating process proceeds to step S303.

(Step S303)

In step S303, the force information determined in step S302 is outputted to the force transmission control unit 21 of the presentation unit 18 so that the force information is transmitted to the hand of the experiencing person 6b. Thereafter, the presentation operating process returns to step S300.

<<Effects of Second Embodiment>>

As described above, since the force can be directly presented to the experiencing person 6b in accordance with the insertion velocity of the guide wire 2a by the determination unit 27, the sensitivity of the total force or the force can be presented in a weak manner at the portion where the operator 6a is inserting the guide wire 2a quickly without paying so much attention, while the sensitivity of the individual force or the force can be presented in a strong manner at the portion where the operator 6a is inserting the guide wire 2a slowly, with much attention being paid.

(Third Embodiment)

Figure 19:
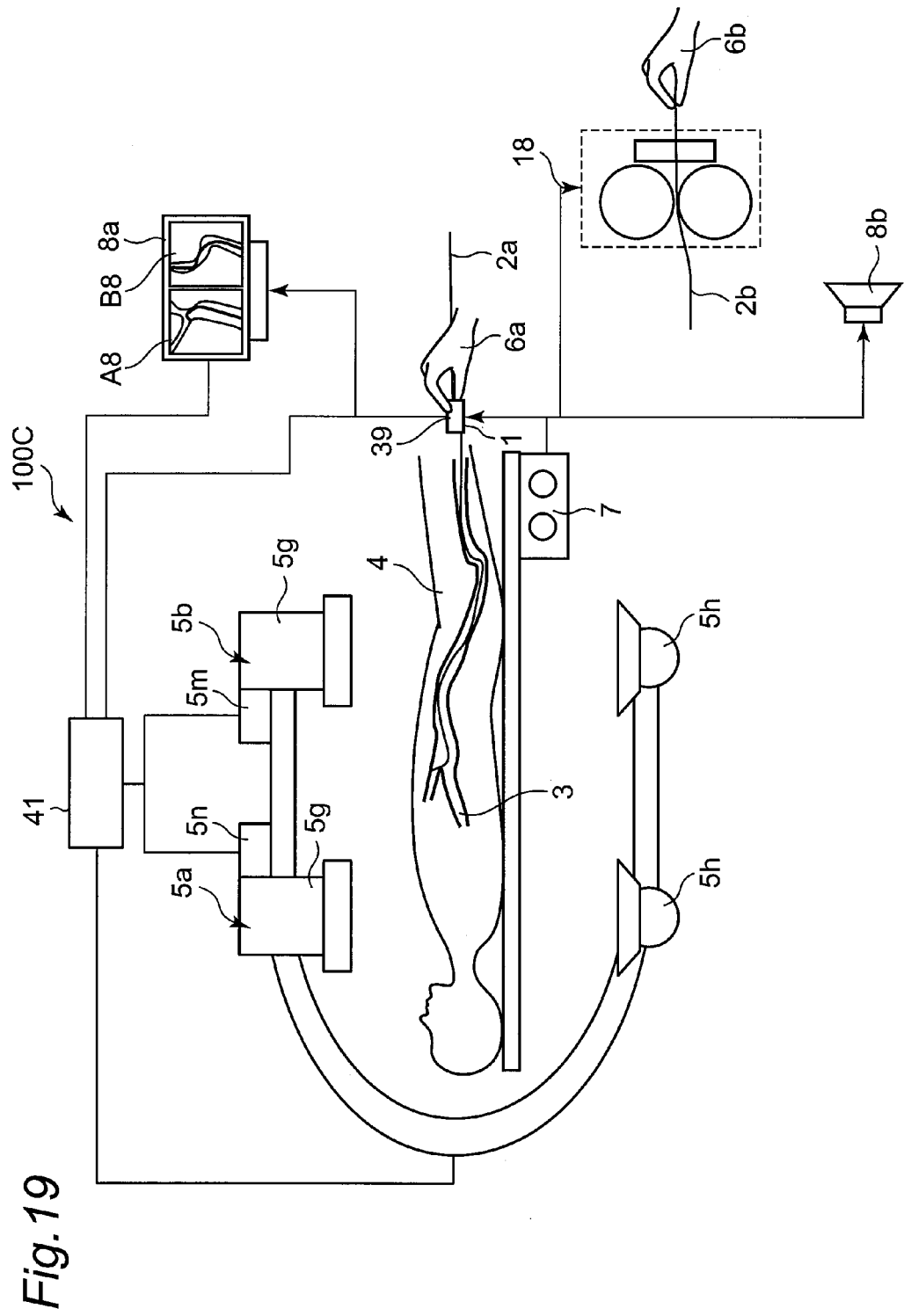
FIG. 19 is a view that shows a schematic configuration of a force presentation system in accordance with a third embodiment of the present invention.
Figure 20:
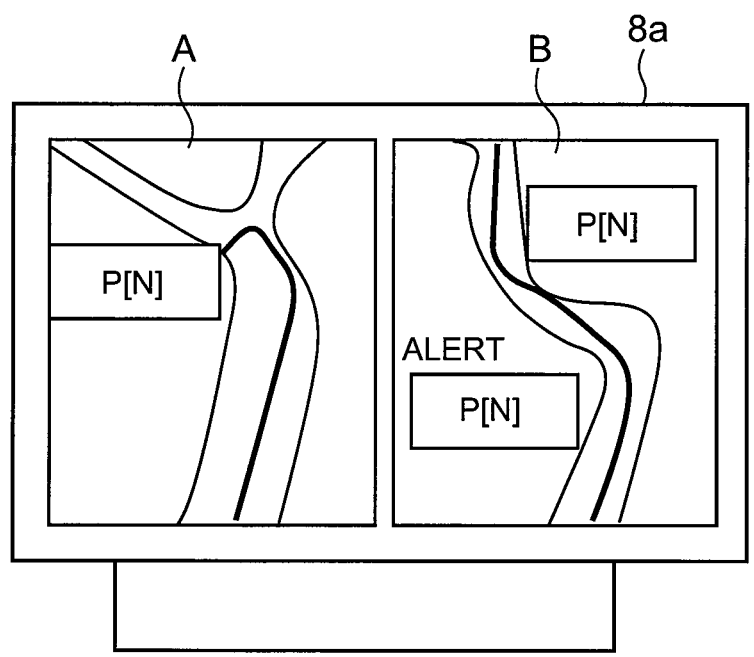
FIG. 20 is a view that explains one example of a notification unit in accordance with the third embodiment of the present invention.

FIG. 19 shows a configuration in which in addition to the device in accordance with the first embodiment, a first X-ray image capture device 5a and a second X-ray image capture device 5b, which serve as one example of the image capture device, capture images of a vascular 3 or a guide wire 2a from the outside of a body and display the captured images on two screens respectively, as shown in FIG. 20, by using a monitor 8a through an image capture device control unit 41 while the operator 6a is inserting the guide wire 2a. On one of the screens (see a left screen A of FIG. 20) of the monitor 8a, a tip portion of the guide wire 2a the image of which is captured by the first X-ray image capture device 5a is displayed, and on the other screen (see a right screen B of FIG. 20), the second X-ray image capture device 5b is controlled to move to a portion of the force transmitted to the experiencing person 6b so that the image of the corresponding portion is displayed. Each of the first X-ray image capture device 5a and the second X-ray image capture device 5b is provided with an X-ray generation unit 5g and an X-ray detection unit 5h relating to the X-ray generation unit 5g in the same manner as in the X-ray image capture device 5 of the first embodiment. Under control by the image capture device control unit 41, the first X-ray image capture device 5a is moved to a predetermined position by a first X-ray image capture device moving unit 5m, while the second X-ray image capture device 5b is moved to another predetermined position by a second X-ray image capture device moving unit 5n. The resulting pieces of image information captured by the first and second X-ray image capture devices 5a and 5b are displayed on the notification unit 8 (monitor 8a), and transmitted from the first and second X-ray image capture devices 5a and 5b and also stored in the measured information database 9 for every predetermined time (for example, every 4 milliseconds) by utilizing the timer 36 via the database input/output unit 14.

Figure 21:
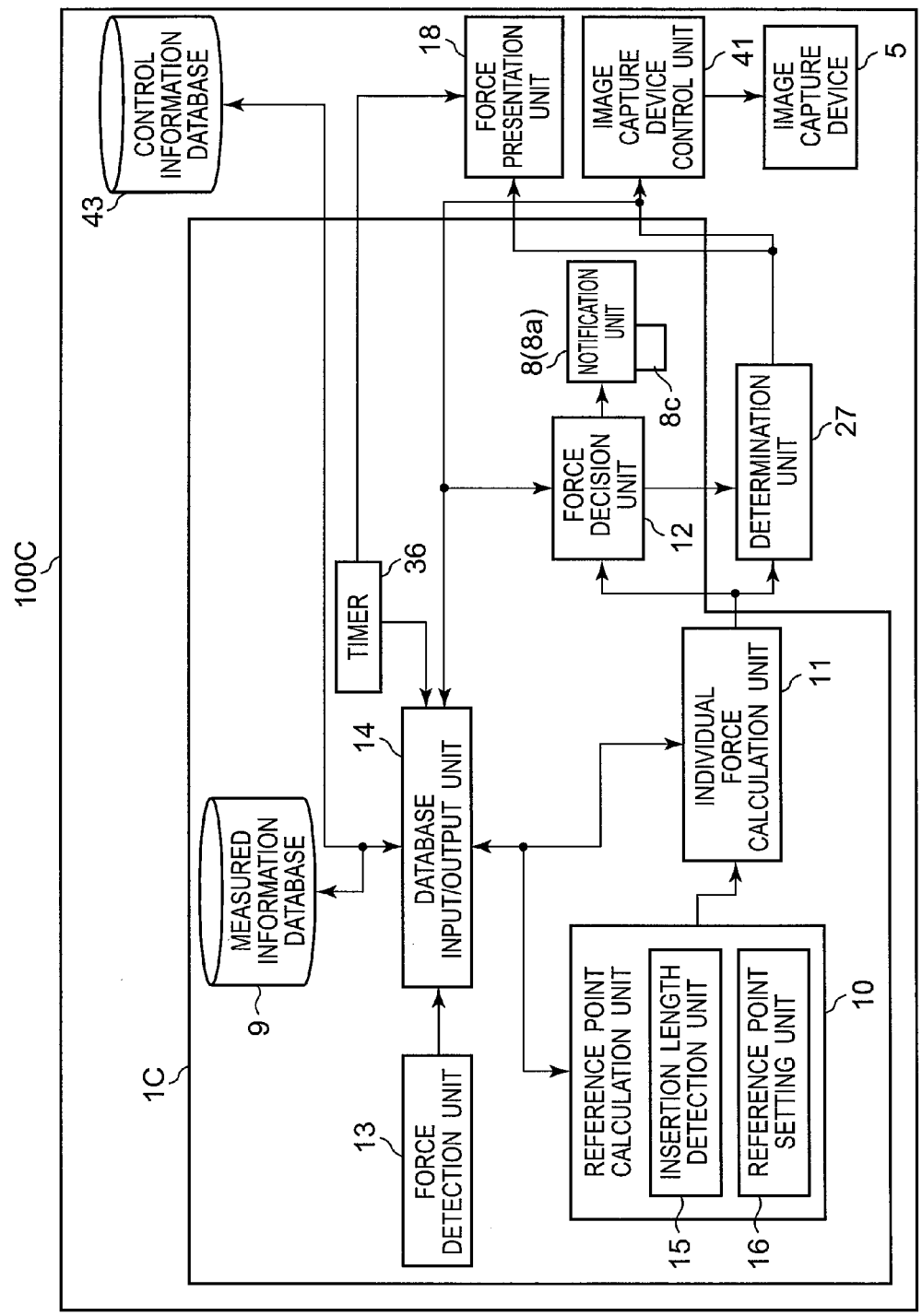
FIG. 21 is a block diagram that shows a detailed configuration of the force presentation system in accordance with the third embodiment of the present invention.

FIG. 21 shows a configuration of a force presentation system 100C. That is, FIG. 21 is a view showing configurations of a force measuring device 1C, the image capture device control unit 41, the first and second X-ray image capture devices 5a and 5b, and a control information database 43 of the third embodiment. Since the force measuring device 1C except for the determination unit 27 has the same structure as that of the first embodiment, the description thereof will be omitted.

<<Determination Unit 27>>

By using the same method as that of the first embodiment, the determination unit 27 determines information (presentation information) relating to forces to be presented on the presentation unit 18 based upon the force detected by the force detection unit 13, the individual forces applied to the respective reference points calculated in the individual force calculation unit 11, and information of the results of decision by the force decision unit 12. The information relating to forces to be presented on the presentation unit 18, determined by the determination unit 27, is outputted to the presentation unit 18, and is also outputted to the image capture device control unit 41.

<<First and Second X-Ray Image Capture Devices 5a and 5b>>

The first and second X-ray image capture devices 5a and 5b irradiate a human body 4 with an X-ray from the outside of the body 4 so that images of vasculars or the guide wire 2a inside the body 4 are captured. The resulting image information captured by the first and second X-ray image capture devices 5a and 5b is displayed on the notification unit 8 (monitor 8a) from the first and second X-ray image capture devices 5a and 5b. For example, as shown by the monitor 8a of FIG. 20, two screens are used for displaying, and one of the screens (see A8 in FIG. 19 as well as A in FIG. 20) displays the tip of the guide wire 2a, and the other screen (see B8 in FIG. 19 as well as B in FIG. 20) displays an image of a portion to which a force determined by the determination unit 27 is applied. The information to be displayed is processed, for example, by an image processing unit 8c that is built in the monitor 8a so that a force P [N], calculated by the force detection unit 13 or the individual force calculation unit 11, is displayed, and upon decision that a load is applied to the vascular 3 by the force decision unit 12, a warning such as "ALERT" or the like is also displayed so as to be recognized.

<<Control Information Database 43>>

As shown in the column of "position of X-ray image capture device" of FIG. 22, the control information database 43 records the position acquired by the image capture device control unit 41 together with information of the measured information database 9 for every predetermined period of time by utilizing the timer 36 via the database input/output unit 14.

<<Database Input/Output Unit 14>>

The database input/output unit 14 carries out data input/output operations among the measured information database 9, the control information database 43, the force detection unit 13, the reference point calculation unit 10, the individual force calculation unit 11, the force decision unit 12, and the image capture device control unit 41.

<<Image Capture Device Control Unit 41>>

Based upon the presentation information determined by the determination unit 27, the image capture device control unit 41 controls the positions of the first and second X-ray image capture devices 5a and 5b, and acquires the current positions (at the measuring point of time) of the image capture devices.

More specifically, in accordance with the insertion task of the guide wire 2a by the operator 6a, the operator 6a or a radiation technician manually shifts the first X-ray image capture device 5a so as to capture the image of the tip of the guide wire 2a. During the insertion task, individual forces are measured by the force measuring device 1C in the same manner as in the first embodiment. The image capture device control unit 41 records the position of the shifted first X-ray image capture device 5a in the control information database 43 together with the information of the measured information database 9. Moreover, the image capture device control unit 41 also controls the first X-ray image capture device 5a so as to display presentation information determined by the determination unit 27 on the monitor 8a.

In this case, the first X-ray image capture device 5a is not controlled because the first X-ray image capture device 5a is shifted by the operator 6a so as to capture the image of the tip of the guide wire 2a. The second X-ray image capture device 5b is drive-controlled by the image capture device control unit 41 so as to capture the image of the portion relating to the presentation information determined in the determination unit 27.

Since the determination unit 27 determines information to be presented to the experiencing person 6b, the second X-ray image capture device 5b captures the image of the portion relating to the information of the force presented to the experiencing person 6b, and allows the monitor 8a to display the resulting image.

More specifically, referring to FIG. 22, an explanation will be given by exemplifying a case in which, when the determination unit 27 determines to present the force corresponding to an individual force $f_{r1}$, the portion relating to the information of the force corresponding to the individual force $f_{r1}$ is image-captured by the second X-ray image capture device 5b, and displayed on the monitor 8a. First, the determination unit 27 calculates the position of the second X-ray image capture device 5b relating to the individual force "$f_{r1}$" based upon the control information database 43.

More specifically, the position of the second X-ray image capture device 5b relating to the individual force "$f_{r1}$" is calculated from the control information database 43. In the example of FIG. 22, the position relating to the individual force "$f_{r1}$" to be image-captured by the second X-ray image capture device 5b corresponds to "$p_{x6}$". Next, a driving control is carried out by the image capture device control unit 41 so that the actual image capturing position of the second X-ray image capture device 5b is located at the position "$p_{x6}$" to be captured, and by shifting the second X-ray image capture device 5b thereto, the corresponding image is captured.

(Presentation Operating Step of Force Presentation System 100C)

Figure 23:
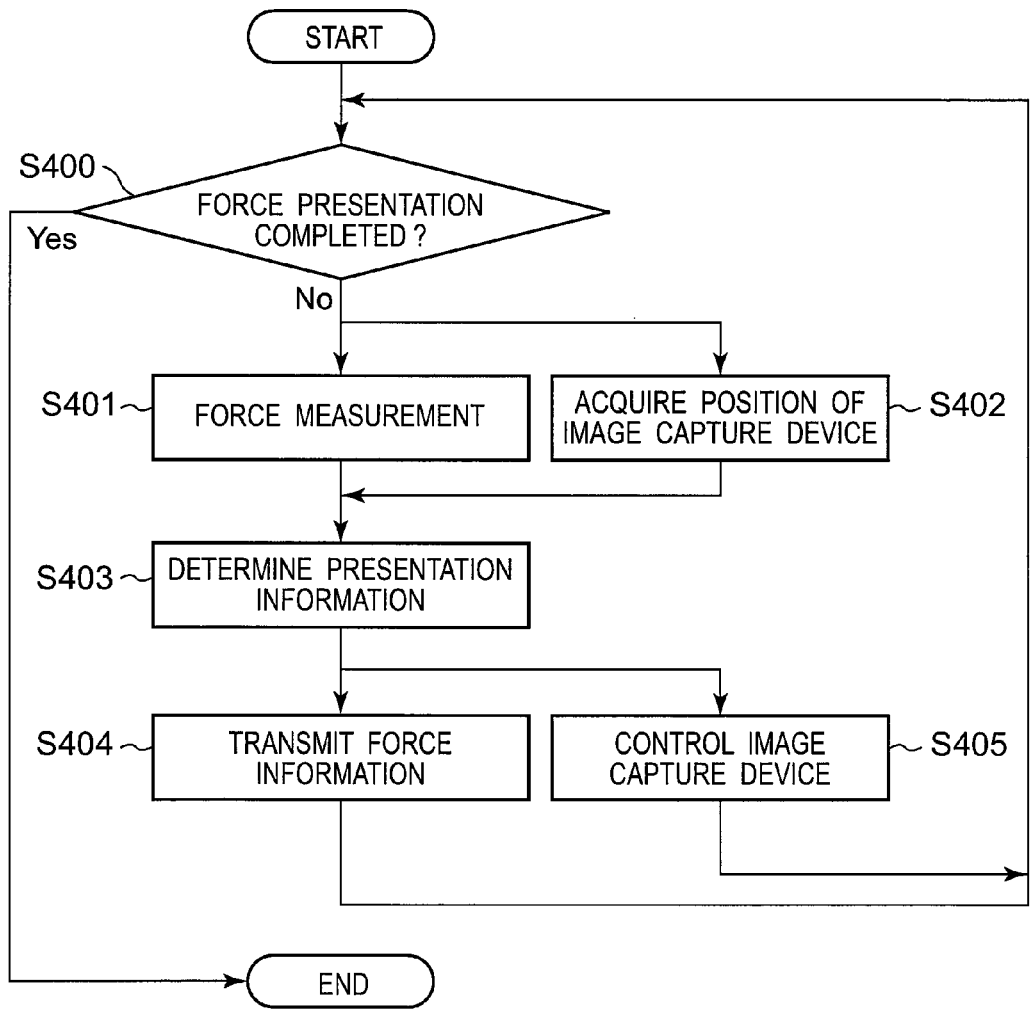
FIG. 23 is a flow chart showing a force presentation system in accordance with the third embodiment of the present invention.

Referring to a flow chart of FIG. 23, the following description will describe a presentation operating step in the force presentation system 100C in accordance with the third embodiment.

(Step S400)

First, upon receipt of starting instructions of force measurements and force presentation from the input IF 7, force measurements are started in the force measuring device 1C through the force measurement control unit 200. In step S400 shown in FIG. 23, in the case where terminating instructions of force measurements and force presentation is given by the input IF 7, the force measurement in the force presentation system 100C and the force presentation in the presentation unit 18 are terminated by the force measurement control unit 200. In the case where no terminating instructions of the force measurements and the force presentation is given, the presentation operating process proceeds to step S401 and S402.

(Step S401)

Next, in step S401, the force measuring device 1C individually measures a contact force at the time when the guide wire 2a is made in contact with a vascular 3 or a frictional force at the time when the guide wire 2a is made in contact with a meandering portion 3a or a branched portion 3b of the vascular 3, while the operator 6a is inserting the guide wire 2a. Since the measuring method is the same as that in the first embodiment, the description thereof will be omitted. Thereafter, the presentation operating process proceeds to step S403.

(Step S402)

Moreover, simultaneously with step S401, the image capture device control unit 41 acquires the position of the first X-ray image capture device 5a when the first X-ray image capture device 5a is shifted by the operator 6a, and stores the resulting position in the control information database 43 (step S402). Thereafter, the presentation operating process proceeds to step S403.

(Step S403)

Next, the determination unit 27 determines information (presentation information) relating to a force to be presented onto the presentation unit 18 based upon the force detected by the force detection unit 13, the individual forces applied to the respective reference points calculated by the individual force calculation unit 11, and the information of the decision result in the force decision unit 12 (step S403). Thereafter, the presentation operating process proceeds to step S404 and S405.

(Step S404)

In step 404, based upon the force information determined so as to be presented in step S403, the corresponding force is outputted to the force transmission device 18 and then transmitted to the hand of the experiencing person 6b. Thereafter, the presentation operating process returns to step S400.

(Step S405)

Simultaneously with step S404, based upon the presentation information determined in the determination unit 27, the image capture device control unit 41 controls the second X-ray image capture device 5b (step S405). Thereafter, the presentation operating process returns to step S400.

<<Effects of Third Embodiment>>

As described above, in addition to the X-ray image of the tip of the guide wire 2a, the X-ray image of a portion to which a force is applied with the force being presented to the experiencing person 6b, can be simultaneously displayed on the monitor 8a. Therefore, the experiencing person 6b is allowed to more easily understand the portion that is being experienced.

(Fourth Embodiment)

Figure 24:
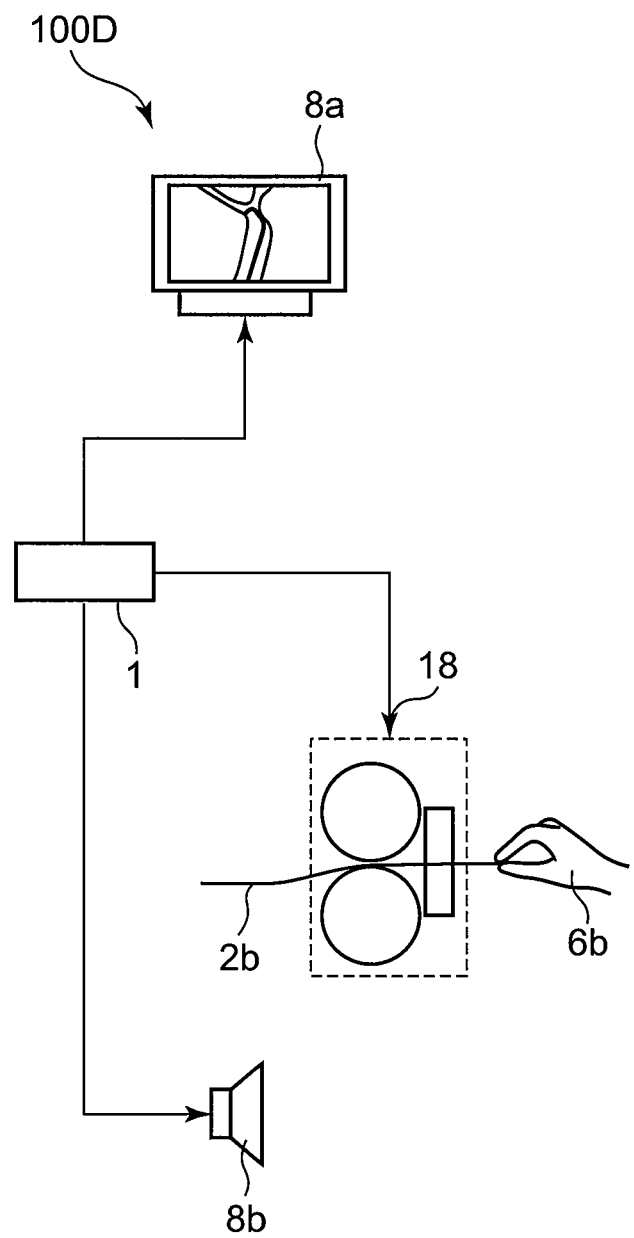
FIG. 24 is a view that shows a schematic configuration of a force presentation system in accordance with a fourth embodiment of the present invention.
Figure 25:
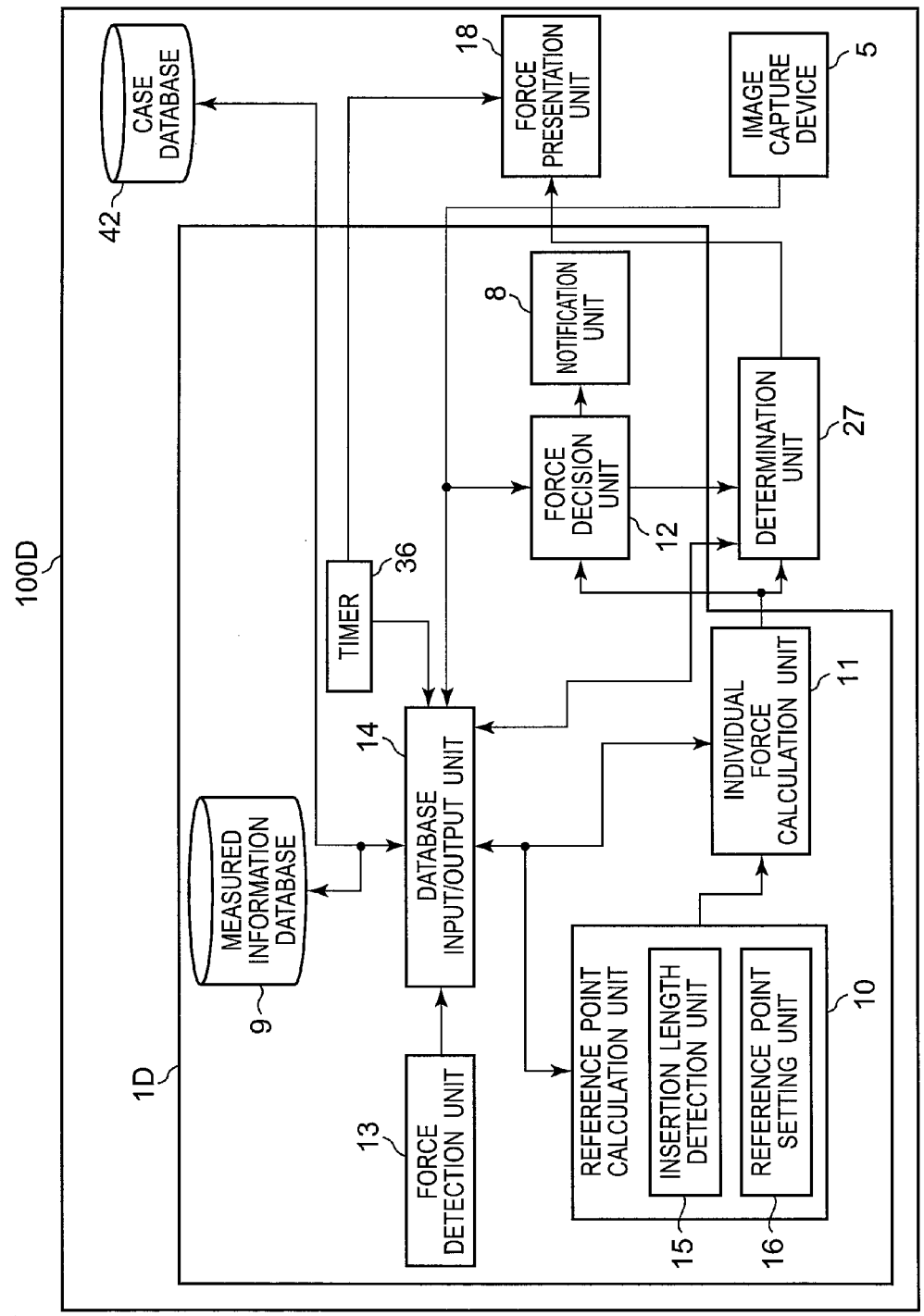
FIG. 25 is a block diagram that shows a detailed configuration of the force presentation system in accordance with the fourth embodiment of the present invention.

FIGS. 24 and 25 show a configuration of a force presentation system 100D in accordance with a fourth embodiment, the force presentation system 100D including a force measuring device 1D, a case database 42, the image capture device 5, and the presentation unit 18. Since, except for the determination unit 27, the force measuring device 1D has the same structure as that of the first embodiment, the description thereof will be omitted. In the fourth embodiment, first, in the same manner as in any one of the force presentation systems 100 to 100C of the first to third embodiments, the operator 6a carries out an inserting task of a guide wire 2a, and the presentation information is preliminarily stored in the database together with the guide wire inserting t. Thereafter, at a later date, in a state where there is no inserting task of the guide wire by the operator 6a, the experiencing person 6b can reproduce information of the guide wire inserting task stored in the database, and experience the presentation operation. This point is a major difference of the fourth embodiment from the first to third embodiments. Therefore, since, in addition to the guide wire inserting task, processes for acquiring the presentation information are the same as those of the processes of any one of the force presentation systems 100 to 100C of the first to third embodiments, most of the explanations will be omitted, with only differences therefrom being mainly explained.

<<Image Capture Device 5 (5a, 5b)>>

In the same manner as in any one of the force presentation systems 100 to 100C of the first to third embodiments, the image capture device 5 (5a, 5b) irradiates a human body 4 with an X-ray from the outside of the body 4 so that images of vasculars 3 or the guide wire 2a inside the body are captured. The resulting image information captured by the image capture device 5 of any one of the force presentation systems 100 to 100C of the first to third embodiments is displayed on the notification unit 8 (monitor 8a), and also stored in the measured information database 9 for every predetermined time (for example, every 4 milliseconds) by utilizing the timer 36 from the image capture device 5 (5a, 5b) through the database input/output unit 14, and simultaneously as these processes are carried out, the corresponding information is also stored in the case database 42.

<<Case Database 42>>

The case database 42 functions as one example of a case data storing unit, and records an X-ray image or an ID indicating an X-ray picture image, captured by the image capture device 5 (5a, 5b), together with information of the measured information database 9, as indicated by the column of "X-ray image" in FIG. 26. For example, the ID is given as an ID that can uniquely identify a file name (for example, x1, x2, . . . ) or the like of an X-ray image or the X-ray video image.

<<Database Input/Output Unit 14>>

The database input/output unit 14 carries out input and output processes of data among the measured information database 9, the force detection unit 13, the reference point calculation unit 10, the individual force calculation unit 11, the force decision unit 12, and the image capture device 5 (5a, 5b).

—Presentation Unit 18—

Figure 27:
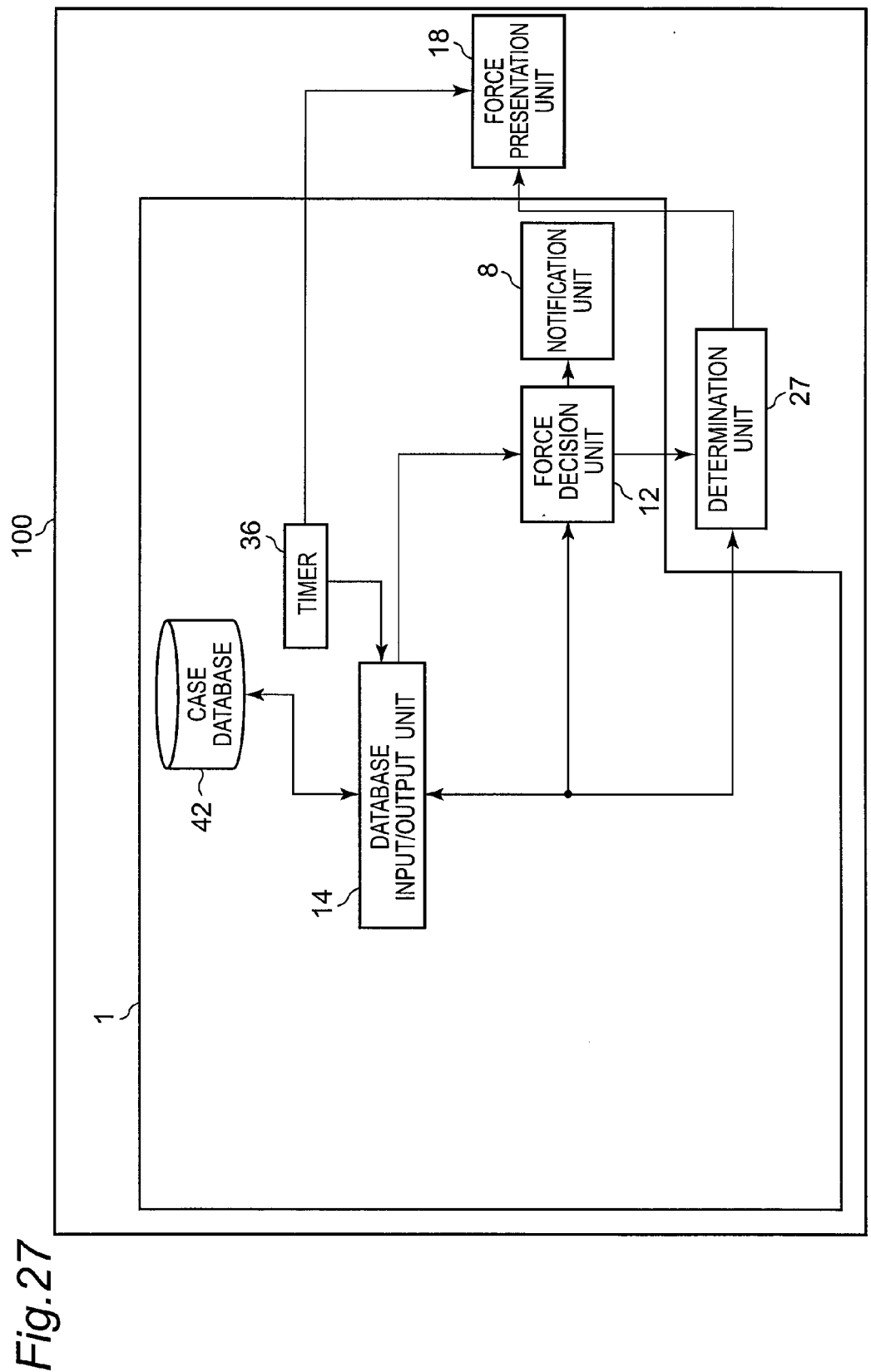
FIG. 27 is a block diagram that shows a detailed configuration of the force presentation system in accordance with the fourth embodiment of the present invention.

In the same manner as in the first embodiment and the like, the presentation unit 18 presents a force to the experiencing person 6b based upon the presentation information outputted from the determination unit 27. Moreover, as shown in FIGS. 24 and 27, at a later date, in the case where only the presentation operation is carried out in a state where there is no inserting task of the guide wire, the information to be presented is outputted onto the force presentation apparatus 18 by the determination unit 27 by using the case database 42 in which the presentation information has been preliminarily stored, so that the force can be presented to the experiencing person 6b by the force presentation apparatus 18. With this arrangement, with respect to even a rare medical case or a medical case having only few examples, off-line practices can be carried out for educating interns and the like attending as the experiencing persons 6b.

(Presentation Operation Acquiring Step of Force Presentation System 100D)

Figure 28:
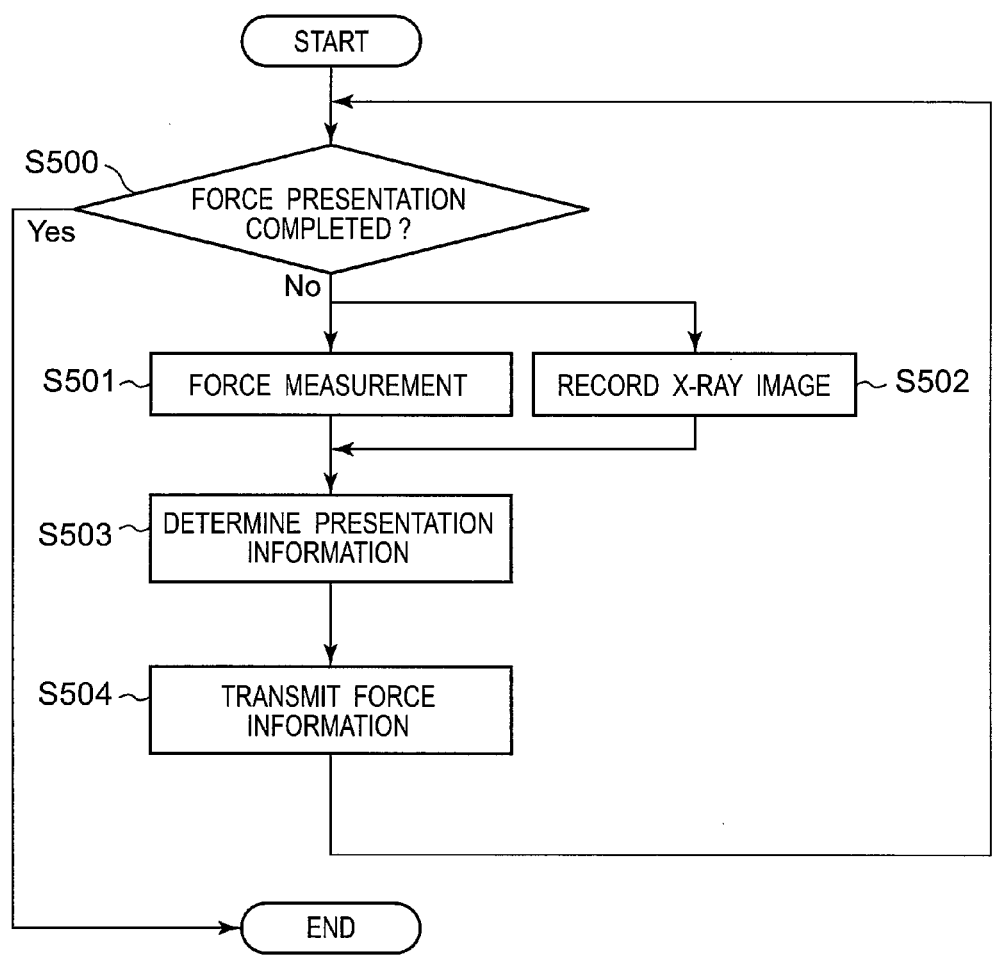
FIG. 28 is a flow chart showing a force presentation system in accordance with the fourth embodiment of the present invention.

Referring to a flow chart of FIG. 28, the following description will describe a presentation operating step of a force presentation system 100D of a fourth embodiment.

(Step S500)

Upon receipt of starting instructions of force measurements and force presentation from the input IF 7, force measurements are started in the force measuring device 1D through the force measurement control unit 200. In step S500 in FIG. 28, in the case where terminating instructions of force measurements and force presentation is given by the input IF 7, the force measurement in the force presentation system 100D and the force presentation in the force presentation unit 18 are terminated through the force measurement control unit 200. In the case where no terminating instructions of the force measurements and the force presentation is given, the presentation operating process proceeds to step S501 and S502.

Next, in step S501, the force measuring device 1D individually measures a contact force at the time when the guide wire 2a is made in contact with a vascular 3 or a frictional force at the time when the guide wire 2a is made in contact with a meandering portion 3a or a branched portion 3b of the vascular 3, while the operator 6a is inserting the guide wire 2a. Since the measuring method is the same as that in the first embodiment, the description thereof will be omitted. Thereafter, the presentation operating process proceeds to step S503.

(Step S502)

Moreover, simultaneously with step S501, an X-ray image captured by the X-ray image capture device 5 is stored in a case database 42. Additionally, the force information in step S501 and the image information in step S502 are made synchronous to each other by instructions from the timer 36. Thereafter, the presentation operating process proceeds to step S503.

(Step S503)

Next, the determination unit 27 determines information relating to a force to be presented onto the presentation unit 18 based upon the force detected by the force detection unit 13, the individual forces applied to the respective reference points calculated by the individual force calculation unit 11, and the information of the decision result in the force decision unit 12. Thereafter, the presentation operating process proceeds to step S504.

(Step S504)

Information relating to a force to be presented onto the presentation unit 18 determined by the determination unit 27 is stored in the case database 42 through the database input/output unit 14. Thereafter, the presentation operating process returns to step S500.

(Presentation Operation Experiencing Step of Force Presentation System 100D)

Figure 29:
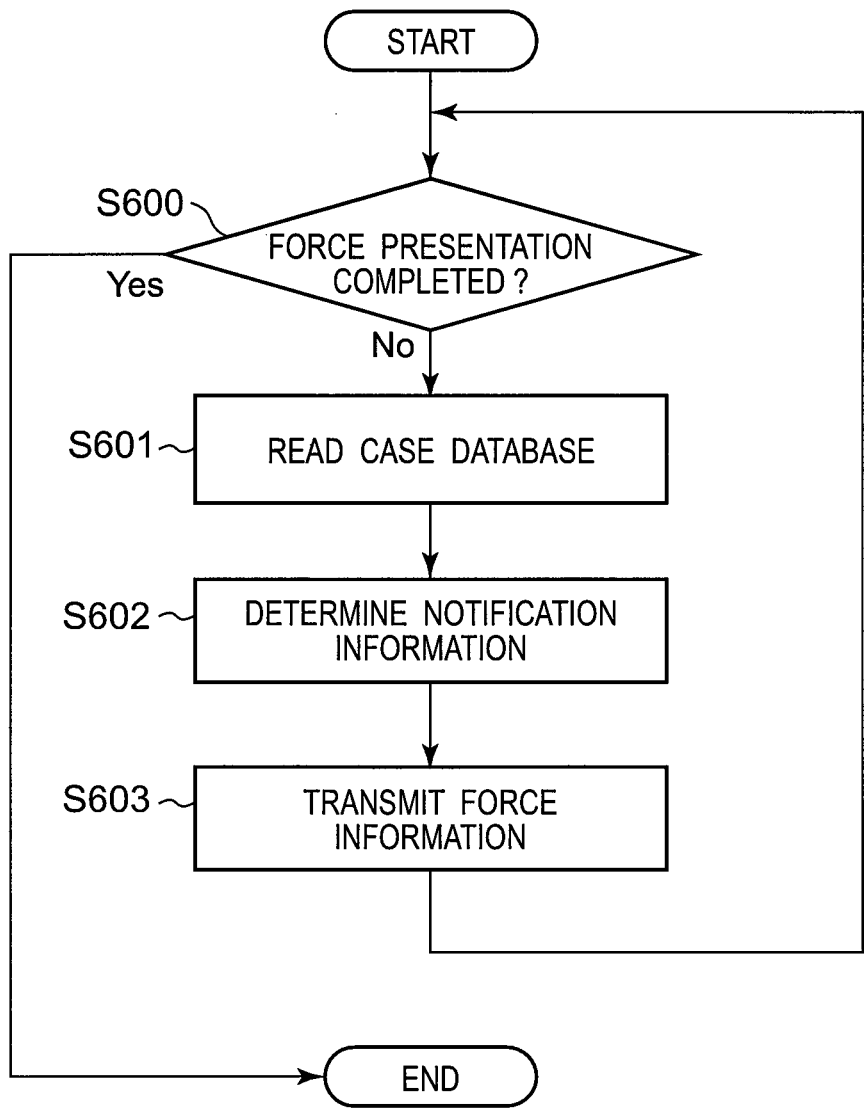
FIG. 29 is a flow chart showing a force presentation system in accordance with the fourth embodiment of the present invention.

As described earlier, after the presentation information has been stored in the case database 42 and then acquired, and at a later date, when an experiencing person 6b attempts to experience the presentation operation, the presentation information is outputted from the case database 42 to the force transmission device 18 through the determination unit 27, and transmitted to the hand of the experiencing person 6b in synchronism with the X-ray image. FIG. 29 shows a flow chart that is used in the case where, as shown in FIGS. 24 and 27, the information to be notified is determined by the determination unit 27 by using the case database 4 that has already stored, and the corresponding force is presented to the experiencing person 6b.

(Step S600)

Upon receipt of starting instructions for a force presentation by the input IF 7, a force measuring operation in the force measuring device 1D is started through the force measurement control unit 200. In step S600 in FIG. 29, upon receipt of terminating instructions for the force presentation from the input IF 7, the force presentation onto the force presentation unit 18 in the force presentation system 100D is terminated through the force measurement control unit 200. In the case of no terminating instructions for the force presentation, the presentation operating process proceeds to the next step S601.

(Step S601)

Next, in step S601, a read-out operation by the determination unit 27 is carried out on the case database 42 that has already been recorded. Thereafter, the presentation operating process proceeds to step S602.

(Step S602)

Next, the determination unit 27 determines information relating to a force to be presented onto the presentation unit 18 based upon the force detected by the force detection unit 13, the individual forces applied to the respective reference points calculated by the individual force calculation unit 11, and the information of the decision result in the force decision unit 12. Thereafter, the presentation operating process proceeds to step S603. That is, in this case, each time an experiencing process is carried out, the presentation information is determined. For example, the presentation information is preliminarily stored in the case database 42, and only its sensitivity can be altered depending on experiencing persons.

(Step S603)

In step S603, force information determined by the determination unit 27 so as to be presented in step S602 is outputted from the determination unit 27 to the force transmission device 18, and transmitted to the hand of the experiencing person 6b in synchronism with the display of the X-ray image on the monitor 8a based upon the timer 36 (database input/output unit 14). Thereafter, the presentation operating process returns to step S600.

Additionally, another structure may be used in which, upon presenting a force by the presentation unit 18 based upon the case database 42 and the determination unit 27, the degree of preference of presentation information is preliminarily stored in the case database 42 together with the presentation information, and only the presentation information having a high degree of preference may be selected by the determination unit 27 and presented onto the presentation unit 18. More specifically, in the case of database 42 shown in FIG. 30, the degree of preference is recorded in the column of "degree of preference". For example, presentation information having the degree of preference "1" is preferentially presented by the determination unit 27, while presentation information having the degree of preference "2" is prevented from being presented by the determination unit 27. Thus, portions where a difficult medical procedure is not required or portions that are not suitable for practices of the experiencing person 6b, such as portions where even the operator 6a requires tries and errors or special preparations or the like, may be stored in the case database 42 with a decreased degree of preference so as not to be presented to the experiencing person 6b. Alternatively, in contrast, in the case where the experiencing person 6b is a person of a catheter manufacturer, the degree of preference may be prepared so as to allow only portions required for the operations of members attached to the catheter (for example, stent insertions or balloon expansions) to be force-transmitted. By setting such degree of preference, it is possible to allow the experiencing person 6b to effectively take (experience) practices.

<<Effects of Fourth Embodiment>>

As described above, by recording the force and the X-ray image at the time of insertion by the operator 6a in the case database 42, an experiencing person 6b can confirm the insertion in synchronism with the X-ray image while feeling the force of the operator 6a by using the case database 42, even when the operator 6a is not present.

<<Modified Examples of Respective Embodiments>>

Additionally, in the first to fourth embodiments, the reference point calculation unit 10 or the force decision unit 12 has a predetermined threshold value (first threshold value, second threshold value, third threshold value, or fourth threshold value); however, as shown in FIG. 31, the threshold value may be altered in accordance with the insertion length. Moreover, the threshold value may be individually corrected depending on a treatment method or a patient (human body 4). With these arrangements, in the case where a guide wire 2a is inserted from a vascular 3 at the root of a leg, since the vascular 3 becomes narrower as the guide wire 2a is inserted, for example, a method is proposed in which the threshold value can be made larger at the time when the guide wire 2a is first inserted, while the threshold value can be made smaller, as the insertion of the guide wire proceeds because the vascular 3 becomes narrower.

Moreover, in the first to fourth embodiments, the reference point calculation unit 10 calculates, as reference points, points of time at which a displacement of force is a predetermined threshold value or more for each predetermined insertion length, and the individual force calculation unit 11 divides values obtained by subtracting the force information at the reference point immediately before from the force information at the respective reference points, by the number of the reference points that have been set before, and the resulting divided value is evenly added to each of individual forces at the respective reference points. Accordingly, individual values are thus calculated. Another method different from this method may be used in which reference points are set for every predetermined period of time, and upon adding the value divided by the number of the reference points that have been set before evenly to each of individual forces at the respective reference points, the value may be added only to the force at each of the reference points with a force having a predetermined threshold value or more.

Furthermore, the individual force calculation unit 11 divides values obtained by subtracting the force information at the reference point immediately before from the force information detected by the force detection unit 13, by the number of the reference points that have been set before, and the resulting divided value is evenly added to each of individual forces at the respective reference points. Accordingly, individual values are thus calculated. However, another method may be used in which the value to be added is given not evenly, but may be changed individually in accordance with the amount of shift of the tip of the guide wire 2a. For example, in the case where the tip of the guide wire 2a is shifted by the same amount as the insertion amount of the tip of the guide wire 2a, it is defined that the individual force at the reference point so far is not changed, and that a value obtained by subtracting the force information at the reference point immediately before from the force information detected by the force detection unit 13 is set as an individual force at a newly added reference point.

Moreover, although the reference points are automatically calculated by the reference point calculation unit 10, the reference point may be given, for example, as a point of time at which the guide wire has passed through a meandering portion 3a of the vascular 3 or at which the guide wire has passed through a branched portion 3b of the vascular 3, or the reference point may be set by the operator 6a.

Furthermore, in the respective embodiments, the force is multiplied by predetermined times by the determination unit 27 so as to be altered, and presented to the experiencing person 6b by using the presentation unit 18; however, in accordance with the degree of skill of the experiencing person 6b, the scale factor of the fixed times may be altered. In the case where the degree of skill is improved, for example, by experiencing many surgeries, the figure of the fixed times may be set lower so that it is possible to present the same force as that is being felt by the operator 6a to the experiencing person 6b.

In the respective embodiments, only the insertion direction has been explained; however, with respect to the rotation direction around the insertion direction, measurements may be carried out by using the same method.

Moreover, in the respective embodiments, the operator 6a is a medical doctor who is qualified to carry out a medical procedure for inserting a catheter, and the experiencing person 6b includes a medical doctor who is qualified to carry out the medical procedure for inserting a catheter, a student such as an intern or a medical student, a person of a catheter manufacturer, or an ordinary person of a company, or the like.

Furthermore, in the respective embodiments, explanations have been given by exemplifying the insertion of a catheter; however, the invention relates to a method for individually calculating a force at the time when a linear member is made in contact with a pipe upon inserting the linear member to the pipe, and the same effects are exerted also in an endoscope inspection for a human body, an industrial endoscope inspection, or the like.

Though the present disclosure has been described above based on the above first to fourth embodiments, the present disclosure should not be limited to the above-described first to fourth embodiments. For example, the present invention also includes the following cases.

Part or entirety of each of the above-described apparatuses is actually a computer system that includes, for example, a microprocessor, ROM, RAM, hard disk unit, display unit, keyboard, mouse, and the like. A computer program is stored on the RAM or the hard disk unit. Functions of each of the apparatuses can be achieved by the microprocessor operating according to the computer program. The computer program mentioned here is a combination of a plurality of instruction codes that indicate commands to a computer for achieving predetermined functions.

For example, each component can be implemented as a result that a program executing section (part/unit) such as a CPU reads and executes software programs recorded in a recording medium such as a hard disk or semiconductor memory. Here, software that implements a part or entirety of the apparatus according to each of the above-mentioned embodiments is a following program. That is to say, this program has a computer execute the sections (parts/units) defined in claims. The program has a computer execute the units/steps defined in claims. That is, such a program is a computer-readable recording medium including a force presentation program for allowing a computer to function as:

a determination unit that determines a force to be transmitted to an experiencing person based upon a force measured by a force measuring unit that detects a force individually applied to each of portions of the living body vessel by an insertion member when an operator inserts the insertion member into the living body vessel, from outside of the living body vessel in time series;

a presentation unit that transmits the force determined by the determination unit to the experiencing person; and a force transmission control unit that controls strength of the force to be transmitted by the presentation unit to the experiencing person and timing of switching the strength of the force based upon information of results of measurement in the force measuring unit in time series.

In addition, it may be possible to execute the program by downloading it from a server or reading it from a predetermined storage medium (an optical disc such as a CD-ROM, a magnetic disc, a semiconductor memory, or the like).

Further, one or more computers can be used to execute the program. That is, centralized processing or distributed processing can be performed.

By properly combining the arbitrary embodiment(s) or modification(s) of the aforementioned various embodiments and modifications, the effects possessed by the embodiment(s) or modification(s) can be produced.

The entire disclosure of Japanese Patent Application No. 2012-224093 filed on Oct. 9, 2012, including specification, claims, drawings, and summary are incorporated herein by reference in its entirety.

INDUSTRIAL APPLICABILITY

The present invention is effectively used for a force presentation apparatus that measures a force exerted at the time when an operator is inserting an insertion member into a living body vessel to present the force to an experiencing person, as well as a force presentation method and a force presentation program for use in the device.

Although the present disclosure has been fully described in connection with the embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A force presentation apparatus comprising:
a force measuring unit that measures a force individually applied to each of portions of a living body vessel by an insertion member when a first user inserts the insertion member into the living body vessel, from outside of the living body vessel in time series;
a determination unit that determines a force to be transmitted to a second user based upon the force measured by the force measuring unit;
a presentation unit that transmits the force determined by the determination unit to the second user; and
a force transmission control unit that controls strength of the force to be transmitted by the presentation unit to the second user and timing of switching the strength of the force based upon information of results of measurement in the force measuring unit in time series;

wherein the force measuring unit comprises:
a force detection unit that detects a force applied to the entire living body vessel by the insertion member, from the outside of the living body vessel;
a point-of-time calculation unit that individually measures a point of time at which the force is applied by the insertion member to the living body vessel, based upon the force detected by the force detection unit; and
an individual force calculation unit that individually calculates a force to be applied by the insertion member to the living body vessel,
wherein upon insertion of the insertion member into the living body vessel, the point-of-time calculation unit sets a point of time at which a displacement of the force becomes not smaller than a predetermined displacement deciding threshold value for every predetermined insertion length, and
the individual force calculation unit divides a value obtained by subtracting information of the force at the point of time immediately before, from information of the force detected by the force detection unit at a measuring point of time, by a number of the points of time that have been set up to the measuring point of time, and adds the resulting divided value to each of individual forces at the respective points of time.

2. The force presentation apparatus according to claim 1, wherein the determination unit determines so as to present the force to be applied by the insertion member to the entire living body vessel (i) in a case where an individual force applied to the living body vessel is less than a predetermined individual force deciding threshold value, and also determines so as to present a force that is individually applied to the living body vessel and has a greatest difference from a predetermined individual force deciding threshold value among the forces individually applied to the living body vessel that have values not lower than the individual force deciding threshold value, (ii) in a case where an individual force applied to the living body vessel is the predetermined individual force deciding threshold value or more.

3. The force presentation apparatus according to claim 1, wherein the determination unit determines so as to present the force to be applied by the insertion member to the entire living body vessel (i) in a case where an insertion velocity upon insertion by the first user is less than a predetermined insertion velocity-use threshold value, and also determines so as to present a force having a greatest difference from the predetermined insertion velocity-use threshold value among the forces individually applied to the living body vessel that have values not lower than the insertion velocity-use threshold value, (ii) in a case where the insertion velocity is the predetermined insertion velocity-use threshold value or more.

4. The force presentation apparatus according to claim 1, wherein the determination unit determines so as to present the force to be applied by the insertion member to the entire living body vessel with a sensitivity lower than the sensitivity of a measured value that is being measured in the force measuring unit (i) in a case where a force individually applied to the living body vessel has a value less than a predetermined sensitivity adjusting threshold value, and the determination unit also determines so as to present the force to be applied by the insertion member to the entire living body vessel with a sensitivity that is increased from a sensitivity of a measured value that is being measured in the force measuring unit (ii) in a case where a force individually applied to the living body vessel has a value that is the predetermined sensitivity adjusting threshold value or more.

5. The force presentation apparatus according to claim 1, wherein the determination unit determines so as to present the force to be applied by the insertion member to the entire living body vessel with a sensitivity lower than a sensitivity of a measured value that is being measured in the force measuring unit (i) in a case where an insertion velocity upon insertion by the first user is less than a predetermined insertion velocity-use threshold value, and the determination unit also determines so as to present the force to be applied by the insertion member to the entire living body vessel with a sensitivity that is increased from a sensitivity of a measured value that is being measured in the force measuring unit (ii) in a case where the insertion velocity is the predetermined insertion velocity-use threshold value or more.

6. The force presentation apparatus according to claim 1, further comprising:
a force decision unit that decides that in a case where force information individually calculated in the individual force calculation unit has a value that is a predetermined load deciding threshold value or more, a load is applied to the living body vessel or the insertion member.

7. The force presentation apparatus according to claim 1, further comprising:
an image capture device that captures an image of a portion where the insertion member is inserted in the living body vessel; and
a notification unit that adds information of a force individually calculated in the individual force calculation unit or information as a result of decision obtained in the force decision unit to a captured image of the living body vessel or the insertion member, and displays the resulting image.

8. The force presentation apparatus according to claim 1, further comprising:
an output unit that informs the first user of information of an individual force calculated in the individual force calculation unit or information as a result of determination given by the force decision unit by means of a sound or an image.

9. The force presentation apparatus according to claim 1, wherein the determination unit determines information to be presented based upon information as a result of decision given by the force decision unit, the device further comprising:
an image capture device that captures an image of a portion where the insertion member is inserted in the living body vessel based upon presentation information determined by the determination unit;
an image capture device control unit that controls the image capture device; and
a notification unit that adds presentation information determined by the determination unit to an image captured by the image capture device and displays the resulting image, under control of the image capture device control unit.

10. A force presentation apparatus comprising:
a force measuring unit that measures a force individually applied to each of portions of a living body vessel by the insertion member when a first user inserts the insertion member into the living body vessel, from outside of the living body vessel in time series;
a determination unit that decides a force to be transmitted to a second user based upon the force measured by the force measuring unit;
a presentation unit that transmits the force determined by the determination unit to the second user;

a force transmission control unit that controls strength of the force to be transmitted by the presentation unit to the second user and timing of switching the strength of the force based upon information of results of measurement in the force measuring unit in time series;

an image capture device that captures an image of a portion where the insertion member is inserted in the living body vessel; and a case data storing unit that stores a force applied by the insertion member to the entire living body vessel or a force individually applied to the living body vessel, measured by the force measuring device upon operation by the first user, and an image of the living body vessel or the insertion member captured by the image capture device as a pair, wherein the determination unit determines a force to be transmitted to the second user based upon the force stored in the case data storing unit, wherein the force measuring unit comprises:

a force detection unit that detects a force applied to the entire living body vessel by the insertion member, from the outside of the living body vessel;

a point-of-time calculation unit that individually measures a point of time at which the force is applied by the insertion member to the living body vessel, based upon the force detected by the force detection unit; and an individual force calculation unit that individually calculates a force to be applied by the insertion member to the living body vessel, wherein upon insertion of the insertion member into the living body vessel, the point-of-time calculation unit sets a point of time at which a displacement of the force becomes not smaller than a predetermined displacement deciding threshold value for every predetermined insertion length, and the individual force calculation unit divides a value obtained by subtracting information of the force at the point of time immediately before, from information of the force detected by the force detection unit at a measuring point of time, by a number of the points of time that have been set up to the measuring point of time, and adds the resulting divided value to each of individual forces at the respective points of time.

11. A force presentation method comprising:

measuring, by a force measuring unit, a force individually applied to each of the portions of a living body vessel by the insertion member when a first user inserts the insertion member into the living body vessel, from outside of the living body vessel in time series;

determining, by a determination unit, a force to be transmitted to the second user based upon the force measured by the force measuring unit;

transmitting the force determined by the determination unit to the second user, by a presentation unit; and controlling, by a control unit, strength of a force to be transmitted by the presentation unit to the second user and timing of switching the strength of the force based upon information of results of measurement in the force measuring unit in time series, wherein the measuring by the force measuring unit comprises:

detecting a force applied to the entire living body vessel by the insertion member, from the outside of the living body vessel;

measuring a point of time at which the force is applied by the insertion member to the living body vessel, based upon the detected force; and individually calculating a force to be applied by the insertion member to the living body vessel, wherein upon insertion of the insertion member into the living body vessel, setting a point of time at which a displacement of the force becomes not smaller than a predetermined displacement deciding threshold value for every predetermined insertion length, and dividing a value obtained by subtracting information of the force at the point of time immediately before, from information of the force detected by the force detection unit at a measuring point of time, by a number of the points of time that have been set up to the measuring point of time, and adding the resulting divided value to each of individual forces at the respective points of time.

12. A computer-readable recording medium including a force presentation program for allowing a computer to function as:

a determination unit that determines a force to be transmitted to a second user based upon a force measured by a force measuring unit that detects a force individually applied to each of portions of a living body vessel by an insertion member when a first user inserts the insertion member into the living body vessel, from outside of the living body vessel in time series;

a presentation unit that transmits the force determined by the determination unit to the second user; and a force transmission control unit that controls strength of the force to be transmitted by the presentation unit to the second user and timing of switching the strength of the force based upon information of results of measurement in the force measuring unit in time series, wherein the force measuring unit comprises:

a force detection unit that detects a force applied to the entire living body vessel by the insertion member, from the outside of the living body vessel;

a point-of-time calculation unit that individually measures a point of time at which the force is applied by the insertion member to the living body vessel, based upon the force detected by the force detection unit; and an individual force calculation unit that individually calculates a force to be applied by the insertion member to the living body vessel, wherein upon insertion of the insertion member into the living body vessel, the point-of-time calculation unit sets a point of time at which a displacement of the force becomes not smaller than a predetermined displacement deciding threshold value for every predetermined insertion length, and the individual force calculation unit divides a value obtained by subtracting information of the force at the point of time immediately before, from information of the force detected by the force detection unit at a measuring point of time, by a number of the points of time that have been set up to the measuring point of time, and adds the resulting divided value to each of individual forces at the respective points of time.

13. The force presentation apparatus according to claim 1, wherein the first user is an operator and the second user is an experiencing person.

14. The force presentation apparatus according to claim 10, wherein the first user is an operator and the second user is an experiencing person.

15. The force presentation method according to claim 11, wherein the first user is an operator and the second user is an experiencing person.

16. The computer-readable recording medium including a force presentation program according to claim 12, wherein the first user is an operator and the second user is an experiencing person.

* * * * *